US010555942B2

(12) United States Patent
Tang et al.

(10) Patent No.: US 10,555,942 B2
(45) Date of Patent: Feb. 11, 2020

(54) EMETINE COMPOUNDS FOR TREATMENT AND PREVENTION OF FLAVIVIRUS INFECTION

(71) Applicants: FLORIDA STATE UNIVERSITY RESEARCH FOUNDATION, INC., Tallahassee, FL (US); THE JOHNS HOPKINS UNIVERSITY, Baltimore, MD (US); The United States of America, as represented by the Secretary, Department of Health and Human Services, Bethesda, MD (US)

(72) Inventors: Hengli Tang, Tallahassee, FL (US); Emily M. Lee, Tallahassee, FL (US); Anil Mathew Tharappel, Tallahassee, FL (US); Hongjun Song, Baltimore, MD (US); Guo-Li Ming, Baltimore, MD (US); Wei Zheng, Rockville, MD (US); Miao Xu, Rockville, MD (US); Shu Yang, Rockville, MD (US); Ruili Huang, Rockville, MD (US); Wenwei Huang, Rockville, MD (US); Khalida Shamim, Gaithersburg, MD (US); Hao Li, Rockville, MD (US)

(73) Assignees: Florida State University Research Foundation, Inc., Tallahassee, FL (US); The Johns Hopkins University, Baltimore, MD (US); The United States of America, as Represented by the Secretary, Department of Health and Human Services, Bethesda, MD (US)

(*) Notice: Subject to any disclaimer, the term of this patent is extended or adjusted under 35 U.S.C. 154(b) by 0 days.

(21) Appl. No.: 16/156,124

(22) Filed: Oct. 10, 2018

(65) Prior Publication Data
US 2019/0105318 A1 Apr. 11, 2019

Related U.S. Application Data

(60) Provisional application No. 62/608,347, filed on Dec. 20, 2017, provisional application No. 62/570,553, filed on Oct. 10, 2017.

(51) Int. Cl.
*A61K 31/4745* (2006.01)
*A61K 45/06* (2006.01)
*A61P 31/14* (2006.01)

(52) U.S. Cl.
CPC .......... *A61K 31/4745* (2013.01); *A61K 45/06* (2013.01); *A61P 31/14* (2018.01)

(58) Field of Classification Search
CPC ...... A61K 31/4745; A61K 45/06; A61P 31/14
See application file for complete search history.

(56) References Cited

U.S. PATENT DOCUMENTS

| | | |
|---|---|---|
| 5,033,252 A | 7/1991 | Carter |
| 5,052,558 A | 10/1991 | Carter |
| 5,323,907 A | 6/1994 | Kalvelage |
| 8,507,498 B2 | 8/2013 | Wabnitz et al. |
| 9,040,529 B2 | 5/2015 | Greff et al. |
| 2005/0203029 A1 | 9/2005 | Schubert et al. |
| 2014/0148377 A1 | 5/2014 | Bakare |
| 2014/0255426 A1 | 9/2014 | Silvestri et al. |
| 2015/0210712 A1 | 7/2015 | Blumberg et al. |
| 2016/0030403 A1 | 2/2016 | Dow et al. |
| 2017/0157219 A1* | 6/2017 | Hodge, III ........... A61K 38/465 |
| 2017/0190700 A1 | 7/2017 | Bakare et al. |
| 2018/0015153 A1 | 1/2018 | Tang et al. |

FOREIGN PATENT DOCUMENTS

| | | |
|---|---|---|
| WO | WO-2006/121467 | 11/2006 |
| WO | WO-2007/002051 | 1/2007 |
| WO | WO-2008/033466 | 3/2008 |
| WO | WO 2009/143297 | 11/2009 |
| WO | WO 2016/004166 | 1/2016 |
| WO | WO 2017/120225 | 7/2017 |
| WO | WO 2017/223491 | 12/2017 |

OTHER PUBLICATIONS

Duffy, M. R. et al. "Zika virus outbreak on Yap Island, Federated States of Micronesia" *N. Engl. J. Med.*, 2009, pp. 2536-2543.
Cao-Lormeau, V. M. et al. "Zika virus, French Polynesia, South Pacific, 2013" *Emerg. Infect. Dis.*, 2014, pp. 1085-1086, vol. 20, No. 6.
Musso, D. "Zika Virus Transmission from French Polynesia to Brazil" *Emerg. Infect. Dis.*, 2015, pp. 1887-1889, vol. 21, No. 10.
Heymann, D. L. et al. "Zika virus and microcephaly: why is this situation a PHEIC?" *Lancet*, 2016, pp. 719-721, vol. 387.
Mlakar, J. et al. "Zika Virus Associated with Microcephaly" *N. Engl. J. Med.*, Mar. 10, 2016, pp. 951-958, vol. 374, No. 10.
Rasmussen, S. A. et al. "Zika Virus and Birth Defects—Reviewing the Evidence for Causality" *N. Engl. J. Med.*, May 19, 2016, pp. 1981-1987, vol. 374, No. 20.

(Continued)

*Primary Examiner* — Sahar Javanmard
(74) *Attorney, Agent, or Firm* — Saliwanchik, Lloyd & Eisenschenk

(57) ABSTRACT

The present invention concerns the use of emetine compounds for the treatment or prevention of Flavivirus infections, such as Zika virus infections. Aspects of the invention include methods for treating or preventing Flavivirus virus infection, such as Zika virus infection, by administering an emetine compound such as emetine or cephaeline, or a combination of two or more emetine compounds, to a subject in need thereof; methods for inhibiting Flavivirus infections such as Zika virus infections in a cell in vitro or in vivo; pharmaceutical compositions; packaged dosage formulations; and kits for treating or preventing Flavivirus infections, such Zika virus infections.

15 Claims, 7 Drawing Sheets

(56) References Cited

OTHER PUBLICATIONS

Cao-Lormeau, V. M. et al. "Guillain-Barré Syndrome outbreak caused by ZIKA virus infection in French Polynesia" *Lancet*, 2016, pp. 1531-1539.
Araujo, L. M. et al. "Guillain-Barre syndrome associated with the Zika virus outbreak in Brazil" *Arq. Neuropsiquiatr.*, 2016, pp. 253-255, vol. 74, No. 3.
Xu, M. et al. "Identification of small-molecule inhibitors of Zika virus infection and induced neural cell death via a drug repurposing screen" *Nature Medicine*, 2016, pp. 1101-1107, vol. 22, No. 10.
Dowall, S. D. et al. "A susceptible mouse model for Zika virus infection" *PloS Negl. Trop. Dis.*, May 5, 2016, pp. 1-13, 10(5):e0004658.
Dudley, D. M. et al. "A rhesus macaque model of Asian-lineage Zika virus infection" *Nature Communications*, 2016, pp. 1-9, vol. 28, No. 7.
Elgart, A. et al. "Improved Oral Bioavailability of BCS Class 2 Compounds by Self Nano-Emulsifying Drug Delivery Systems (SNEDDS): The Underlying Mechanisms for Amiodarone and Talinolol" *Pharm Res.*, 2013, pp. 3029-3044, vol. 30, No. 12.
Elkihel, L. et al. "Synthesis and orally macrofilaricidal evaluation of niclosamide lymphotropic prodrugs," *Arzneimittelforschung*, 1994, pp. 1259-1264, vol. 44, No. 11, Abstract.
Gourinat, A-C et al. "Detection of Zika Virus in Urine" *Emerg. Infect. Dis.*, Jan. 2015, pp. 84-86, vol. 21, No. 1.
Kansara, H. et al. "Techniques used to Enhance Bioavailability of BCS Class II Drugs: A Review," *Int. J. Drug Dev. & Res.*, 2015, pp. 82-93, vol. 7, No. 1.
Khamkar, G. S. "Self micro emulsifying drug delivery system (SMEED) o/w microemulsion for BCS Class II drugs: an approach to enhance oral bioavailability" *International Journal of Pharmacy and Pharmaceutical Sciences*, 2011, pp. 1-3, vol. 3, No. 3.
Koide, F. et al. "Development of a Zika Virus Infection Model in Cynomolgus Macaques" *Frontiers in Microbiology*, 2016, pp. 1-8, vol. 7.
Kuno, G. et al. "Phylogeny of the Genus *Flavivirus*" *Journal of Virology*, Jan. 1998, pp. 73-83, vol. 72, No. 1.
Lasslo, A. et al. "Chemical and Pharmacologic Studies on Emetine and Quaternary Emetine Derivatives" *Journal of the American Pharmaceutical Association*, Jan. 1950, pp. 43-46, vol. 39, No. 1, Abstract.
Lazear, H. M. et al. "A Mouse Model of Zika Virus Pathogenesis" *Cell Host Microbe*, 2016, pp. 720-730, vol. 19, No. 5.
Morrison, T. E. et al. "Animal Models of Zika Virus Infection, Pathogenesis, and Immunity" *J. Virol.*, 2017, pp. 1-15, vol. 91, No. 8.
Musso, D. et al. "Detection of Zika virus in saliva" *J. Clin. Virol.*, 2015, pp. 53-55, vol. 68.
Pyman, F. L. et al. "The Action of Certain Emetine Derivatives on Amoebae" *Journal of Pharmacology and Experimental Therapeutics*, Oct. 1917, pp. 237-241, vol. 10, No. 4.
Reddy, M. S. et al. "Solubility enhancement of fenofibrate, a BCS class II drug, by self emulsifying drug delivery systems" *International Research Journal of Pharmacy*, 2011, pp. 173-177, vol. 2, No. 11.
Rossi, S. L. et al. "Characterization of a Novel Murine Model to Study Zika Virus" *Am. J. Trop. Med. Hyg.*, 2016, pp. 1362-1369, vol. 94, No. 6.
Singh, N. et al. "Techniques for Bioavailability Enhancement of BCS Class II Drugs: A Review" *International Journal of Pharmaceutical and Chemical Science*, 2013, pp. 1092-1101, vol. 2, No. 2.
Asghar, U. et al. "The history and future of targeting cyclin-dependent kinases in cancer therapy" *Nat. Rev. Drug Discov.*, 2015, pp. 130-146, vol. 14, No. 2.
Barreyro, F. J. et al. "The pan-caspase inhibitor Emricasan (IDN-6556) decreases liver injury and fibrosis in a murine model of non-alcoholic steatohepatitis" *Liver Int.*, 2015, pp. 953-966, vol. 35.
Brennand, K. J. et al. "Modelling schizophrenia using human induced pluripotent stem cells" *Nature*, 2011, pp. 221-225, vol. 473.
Chen, C. Z. et al. "High-throughput Giardia lamblia viability assay using bioluminescent ATP content measurements" *Antimicrob. Agents Chemother.*, 2011, pp. 667-675, vol. 55.
Cugola, F. R. et al. "The Brazilian Zika virus strain causes birth defects in experimental models" *Nature*, 2016, pp. 267-271, vol. 534.
Dang, J. et al. "Zika Virus Depletes Neural Progenitors in Human Cerebral Organoids through Activation of the Innate Immune Receptor TLR3" *Cell Stem Cell*, 2016, pp. 258-265, vol. 19, No. 2.
Debnath, A. et al. "A high-throughput drug screen for Entamoeba histolytica identifies a new lead and target" *Nat. Med.*, 2012, pp. 956-960, vol. 18.
Dick, G. W. et al. "Zika virus. I. Isolations and serological specificity" *Trans. R. Soc. Trop. Med. Hyg.*, 1952, pp. 509-520, vol. 46.
Dou, Q. P. et al. "Overview of Proteasome Inhibitor-Based Anticancer Therapies: Perspective on Bortezomib and Second Generation Proteasome Inhibitors versus Future Generation Inhibitors of Ubiquitin-Proteasome System" *Curr. Cancer Drug Targets*, 2014, pp. 517-536, vol. 14, No. 6.
Driggers, R. W. et al. "Zika Virus Infection with Prolonged Maternal Viremia and Fetal Brain Abnormalities" *N. Engl. J. Med.*, 2016, pp. 2142-2151, vol. 374, No. 22.
Fang, J. et al. "Identification of three antiviral inhibitors against Japanese encephalitis virus from library of pharmacologically active compounds 1280" *PLOS ONE*, 2013, pp. 1-8, vol. 8, No. 11, e78425.
Garcez, P. P. et al. "Zika virus impairs growth in human neurospheres and brain organoids" *Science*, 2016, pp. 816-818, vol. 352.
Hamel, R. et al. "Biology of Zika Virus Infection in Human Skin Cells" *J. Virol.*, 2015, pp. 8880-8896, vol. 89.
He, S. et al. "Repurposing of the antihistamine chlorcyclizine and related compounds for treatment of hepatitis C virus infection" *Sci. Transl. Med.*, 2015, pp. 1-12, vol. 7, No. 282, 282ra49.
Huang, R. et al. "The NCGC pharmaceutical collection: a comprehensive resource of clinically approved drugs enabling repurposing and chemical genomics" *Sci. Transl. Med.*, 2011, pp. 1-23, vol. 3, No. 80, 80ps16.
Johansen, L. M. et al. "A screen of approved drugs and molecular probes identifies therapeutics with anti-Ebola virus activity" *Sci. Transl. Med.*, 2015, pp. 1-15, vol. 7, No. 290, 290ra89.
Jurgeit, A. et al. "Niclosamide Is a Proton Carrier and Targets Acidic Endosomes with Broad Antiviral Effects" *PLOS Pathog.*, 2012, pp. 1-14, vol. 8, No. 10, e1002976.
Kouznetsova, J. et al. "Identification of 53 compounds that block Ebola virus-like particle entry via a repurposing screen of approved drugs" *Emerg. Microbes Infect.*, 2014, pp. 1-7, vol. 3, No. 12, e84.
Li, Z. et al. "Existing drugs as broad-spectrum and potent inhibitors for Zika virus by targeting NS2B-NS3 interaction" *Cell Res.*, 2017, pp. 1046-1064, vol. 27.
Li, C. et al. "Zika Virus Disrupts Neural Progenitor Development and Leads to Microcephaly in Mice" *Cell Stem Cell*, 2016, pp. 120-126, vol. 19, No. 1.
Malumbres, M. et al. "CDK inhibitors in cancer therapy: what is next?" *Trends in Pharmacological Sciences*, Epub, Dec. 4, 2007, pp. 16-21, vol. 29, No. 1.
Manasanch, E. E. et al. "Proteasome inhibitors in cancer therapy" *Nature Reviews Clinical Oncology*, 2017, pp. 417-433, vol. 14, No. 7.
Miner, J. J. et al. "Zika Virus Infection during Pregnancy in Mice Causes Placental Damage and Fetal Demise" *Cell*, 2016, pp. 1081-1091, vol. 165.
Mlakar, J. et al. "Zika Virus Associated with Microcephaly" *N. Engl. J. Med.*, 2016, pp. 951-958, vol. 374.
Mook, R. A. et al. "Structure-activity studies of Wnt/β-catenin inhibition in the Niclosamide chemotype: Identification of derivatives with improved drug exposure," *Bioorg. Med. Chem.*, 2015, pp. 5829-5838, vol. 23, No. 17.
Nowakowski, T. J. et al. "Expression Analysis Highlights AXL as a Candidate Zika Virus Entry Receptor in Neural Stem Cells" *Cell Stem Cell*, 2016, pp. 591-596, vol. 18.
Pan, J.-X. et al. "Niclosamide, an antihelminthic agent, demonstrates antitumor activity by blocking multiple signaling pathways of cancer stem cells" *Chin. J. Cancer*, 2012, pp. 178-184, vol. 31, No. 4.

(56) References Cited

OTHER PUBLICATIONS

Pockros, P.J. et al. "Oral IDN-6556, an antiapoptotic caspase inhibitor, may lower aminotransferase activity in patients with chronic hepatitis C" *Hepatology*, 2007, pp. 324-329, vol. 46.
Qian, X. et al. "Brain-Region-Specific Organoids Using Mini-bioreactors for Modeling ZIKV Exposure" *Cell*, 2016, pp. 1238-1254, vol. 165.
Sanchez-Martinez, C. et al. "Cyclin dependent kinase (CDK) inhibitors as anticancer drugs" *Bioorganic & Medicinal Chemistry Letters*, 2015, pp. 3420-3435, vol. 25, No. 17.
Schang, L.M. et al. "Five years of progress on cyclin-dependent kinases and other cellular proteins as potential targets for antiviral drugs," *Antivir. Chem. Chemother.*, 2006, pp. 293-320, vol. 17.
Shiffman, M. L. et al. "Clinical trial: the efficacy and safety of oral PF-03491390, a pancaspase inhibitor—a randomized placebo-controlled study in patients with chronic hepatitis C" *Aliment. Pharmacol. Ther.*, 2010, pp. 969-978, vol. 31.
Sun, W. et al. "Chemical signatures and new drug targets for gametocytocidal drug development" *Sci. Rep.*, 2014, pp. 1-11, vol. 4, vol. 3743.
Sun, W. et al. "Rapid identification of antifungal compounds against Exserohilum rostratum using high throughput drug repurposing screens" *PLOS ONE*, pp. 1-10, vol. 8, No. 8, e70506.
Sun, W. et al. "Drug combination therapy increases successful drug repositioning," *Drug Discov. Today*, 2016, pp. 1189-1195, vol. 21, No. 7.
Tang, H. et al. "Zika Virus Infects Human Cortical Neural Progenitors and Attenuates Their Growth" *Cell Stem Cell*, 2016, pp. 587-590, vol. 18.
Topol, A. et al. "Increased abundance of translation machinery in stem cell-derived neural progenitor cells from four schizophrenia patients" *Transl. Psychiatry*, 2015, pp. 1-12, vol. 5, e662.
Wang, Y. et al. "A grid algorithm for high throughput fitting of dose-response curve data," *Curr. Chem. Genomics*, 2010, pp. 57-66, vol. 4.
Wen, Z. et al. "Synaptic dysregulation in a human iPS cell model of mental disorders" *Nature*, 2014, pp. 414-418, vol. 515.
Wu, C. J. et al. "Inhibition of severe acute respiratory syndrome coronavirus replication by niclosamide" *Antimicrob. Agents Chemother.*, 2004, pp. 2693-2696, vol. 48.
Zhang, J. H. et al. "A Simple Statistical Parameter for Use in Evaluation and Validation of High Throughput Screening Assays" *J. Biomol. Screen.*, 1999, pp. 67-73, vol. 4.
Zheng, W. et al. "Phenotypic screens as a renewed approach for drug discovery" *Drug Discov. Today*, 2013, pp. 1067-1073, vol. 18.
Tomizawa, M. et al. "Niclosamide suppresses hepatoma cell proliferation via the Wnt pathway" *Onco Targets and Therapy*, 2013, pp. 1685-1693, vol. 6.
Berge, S. M. et al. "Pharmaceutical Salts" *Journal of Pharmaceutical Science*, 1977, pp. 1-19, vol. 66, No. 1.
Wu, K-M. "A New Classification of Prodrugs: Regulatory Perspectives" *Pharmaceuticals*, 2009, pp. 77-81, vol. 2, No. 3.
Cheung, Y. Y. et al. "Antiviral activity of lanatoside C against dengue virus infection" *Antiviral Research*, 2014, pp. 93-99, vol. 111.
Toresdahl, B. G. et al. "Update on Zika Virus: Considerations for the Traveling Athlete" *Sports Health*, 2016, pp. 438-443, vol. 8, No. 5.
Craig, N. "Case Report Fish tapeworm and sushi" *Can. Fam. Physician*, 2012, pp. 654-658, vol. 58.

\* cited by examiner

EMETINE COMPOUNDS FOR TREATMENT AND PREVENTION OF FLAVIVIRUS INFECTION

CROSS-REFERENCE TO RELATED APPLICATIONS

The present application claims the benefit of U.S. Provisional Application Ser. No. 62/608,347, filed Dec. 20, 2017, and U.S. Provisional Application Ser. No. 62/570,553, filed Oct. 10, 2017, each of which is hereby incorporated by reference herein in its entirety, including any figures, tables, nucleic acid sequences, amino acid sequences, or drawings.

BACKGROUND OF THE INVENTION

Zika virus (ZIKV), a mosquito-borne flavivirus, has re-emerged and spread across the Western Hemisphere in the past year. First isolated in 1947 from a sentinel rhesus macaque in the Ziika Forest region of Uganda [1], ZIKV had remained in relative obscurity for many years until outbreaks in the Pacific islands and then the Americas in the past decade [2-4]. A large outbreak started in Brazil in late 2014 and is a growing public health concern [5]. Currently, active transmission has been reported in 58 countries and territories globally. About 20% of ZIKV infected individuals develop symptoms, which mostly resemble symptoms caused by other arboviruses, such as dengue viruses or chikungunya virus. Unlike these viruses, however, ZIKV causes congenital defects, including microcephaly [6,7], and is also associated with Guillain-Barré syndrome in infected adults [8,9].

BRIEF SUMMARY OF THE INVENTION

The present invention concerns the use of emetine compounds for the treatment or prevention of Flavivirus infections, such as Zika virus infections. Aspects of the invention include methods for treating or preventing Flavivirus virus infection, such as Zika virus infection, by administering an emetine compound to a subject in need thereof, methods for inhibiting Flavivirus infections such as Zika virus infections in a cell in vitro or in vivo; pharmaceutical compositions; packaged dosage formulations; and kits for treating or preventing Flavivirus infections, such Zika virus infections.

The inventors have identified a novel use for emetine compounds in the treatment and prevention of Zika virus (ZIKV) infections and other Flavivirus infections. In some embodiments, the emetine compound comprises emetine, cephaeline, psychotrine, o-methyl psychotrine, or emetamine, or a prodrug, metabolite, or derivative of any of the foregoing, or a pharmaceutically acceptable salt of any of the foregoing. In some embodiments, the emetine compound comprises cephaeline isoamyl ether or cephaeline ethyl ether, or a prodrug, metabolite, or derivative thereof, or a pharmaceutically acceptable salt of any of the foregoing. In some embodiments, the emetine compound comprises a compound in Table 1, or a prodrug, metabolite, or derivative thereof, or a pharmaceutically acceptable salt of any of the foregoing.

In some embodiments, the emetine compound is administered in combination (simultaneously or sequentially in any order) with an additional agent that is useful for the treatment or prevention of Flavivirus infection, such as Zika virus infection. For example, an additional agent may be selected from among:

(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxyethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

FIG. 9. Zika virus load estimation in mouse serum following emetine treatment before and after Zika virus challenge. Serum was separated. NS1 protein was estimated using ZIKV-NS1 ELISA kit (Biofront, Tallahassee, Fla.) as per the manufacturer's protocol. Briefly, 5 μl of the serum was lysed with equal volume of lysis buffer for 30 min at 37° C. A 1:300 dilution of the serum was done using sample dilution buffer and added to ELISA plates. Reactions were quantified using HRP conjugated antibody and TMB. Absorbance was taken at 450 nm after adding the stop solution. Statistical analysis was done using the Mann-Whitney ANOVA. *p<0.05, p<0.01, *p<0.001.

FIG. 10. Zika virus load estimation in mouse liver following emetine treatment before and after Zika virus challenge. From 30 mg of liver tissue stored in RNAlater (Qiagen), total RNA was isolated using RNeasy mini kit (Qiagen) and converted to cDNA. Viral NS1 gene expression was estimated by real time PC Relative expression of the NS1 gene was calculated using ZIKV-NS1 specific primers and GAPDH primers. Statistical analysis was done using the Mann-Whitney ANOVA. *p<0.05, p<0.01, *p<0.001.

DETAILED DESCRIPTION OF THE INVENTION

The inventors have identified compounds useful for the treatment and prevention of Zika virus (ZIKV) infections and other Flavivirus infections based at least on their ability to inhibit Flavivirus infection in vitro or in vivo.

One aspect of the invention concerns a method for treating or preventing Flavivirus infection in a human or non-human animal subject, said method comprising administering an effective amount of at least one emetine compound to a subject in need thereof. In some embodiments, the Flavivirus is Zika virus.

In some embodiments, the at least one emetine compound comprises emetine, cephaeline, psychotrine, o-methyl psychotrine, or emetamine, or a prodrug, metabolite, or derivative of any of the foregoing, or a pharmaceutically acceptable salt of any of the foregoing. In some embodiments, the at least one emetine compound is cephaeline, or a prodrug, metabolite, or derivative thereof, or a pharmaceutically acceptable salt of any of the foregoing. In some embodiments, the emetine compound comprises cephaeline isoamyl ether, cephaeline ethyl ether, or a prodrug, metabolite, or derivative thereof, or a pharmaceutically acceptable salt of any of the foregoing.

In some embodiments, the at least one emetine compound comprises cephaeline isoamyl ether or cephaeline ethyl ether, or a prodrug, metabolite, or derivative thereof, or a pharmaceutically acceptable salt of any of the foregoing. The chemical structures of cephaeline ethyl ether (KSH010-075) and cephaeline isoamyl ether, which can be synthesized by a Williamson etherification of cephaeline, are shown.

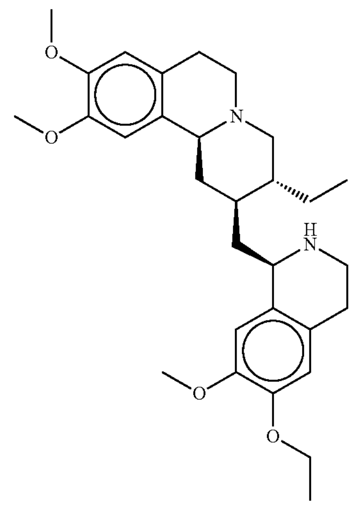

KSH010-075 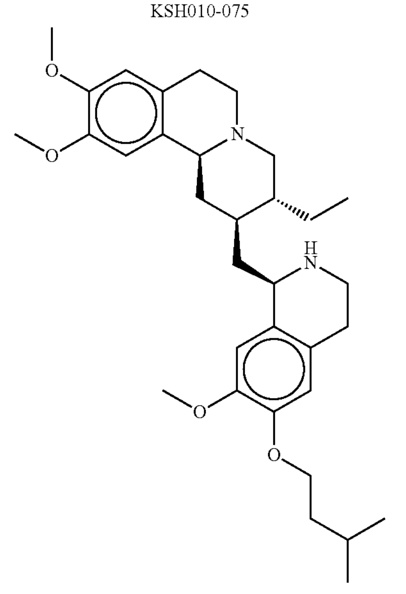 cephaeline isoamyl ether

In some embodiments, the at least one emetine compound is dehydroemetine, or a prodrug, metabolite, or derivative thereof, or a pharmaceutically acceptable salt of any of the foregoing.

In some embodiments, the at least one emetine compound comprises a compound having a structure shown in Table 1, or a prodrug, metabolite, or derivative thereof, or a pharmaceutically acceptable salt of any of the foregoing, which can be prepared by amidation, alkylation, sulfamidation, urea formation, urethane formation, or quaternization of emetine, or carbonation of cephaeline by well established methods in the art.

TABLE 1

Figure 1A:
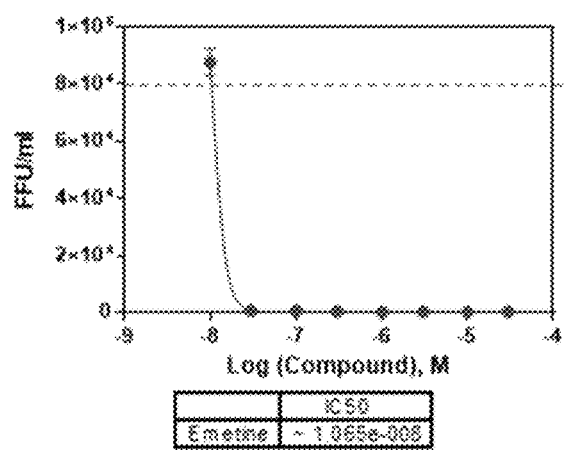
FIGS. 1A-B. Antiviral activity of emetine against ZIKV infection. ZIKV production from human glioblastoma SNB-19 cells treated with increasing concentrations of emetine. 24 hours post-infection, supernatants from SNB-19 cells were titrated onto naïve Vero cells plated in a monolayer in 96-well plates for infectious focus-forming unit assay as previously described and focus forming units quantified [10]. Results are shown in FIG. 1A. The chemical structure of emetine is shown in FIG. 1B.
Figure 1B:
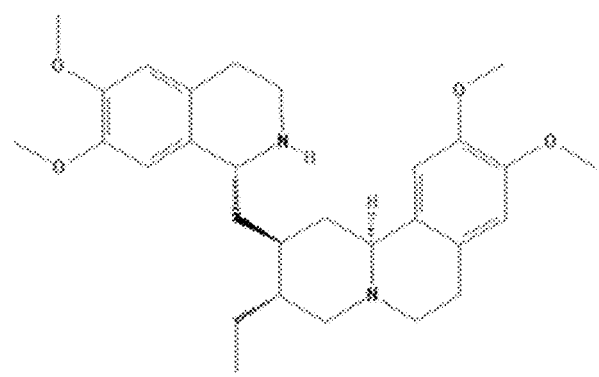
Figure 2A:
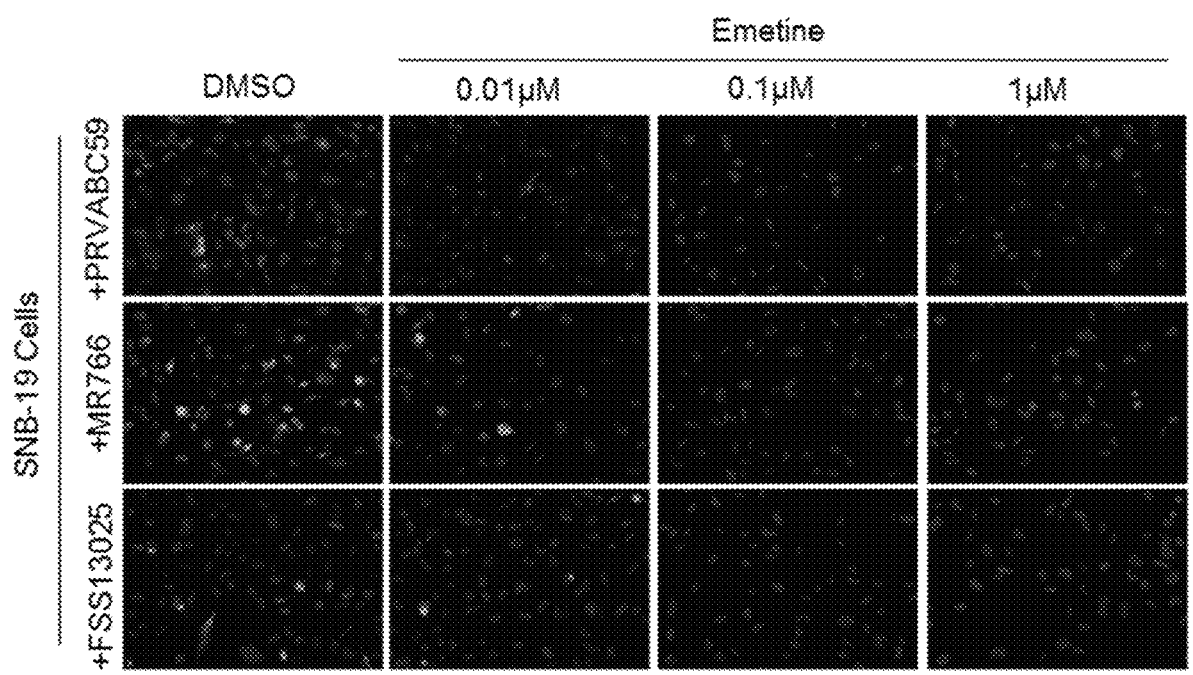
FIGS. 2A-B. Emetine reduces ZIKV infection in a dosage dependent manner. Immunofluorescence (IF) staining (FIG. 2A) and quantification (FIG. 2B) of ZIKV positive SNB-19 cells following infection with one of three ZIKV strains and treatment with emetine at 0.01, 0.1, or 1 µM. Emetine is effective against all three ZIKV strains tested.
Figure 2B:
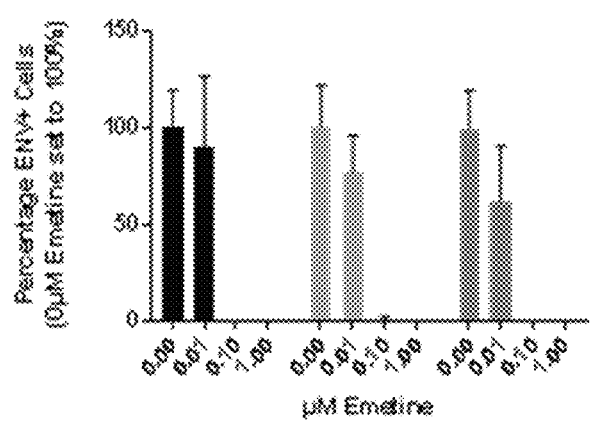
Figure 3:
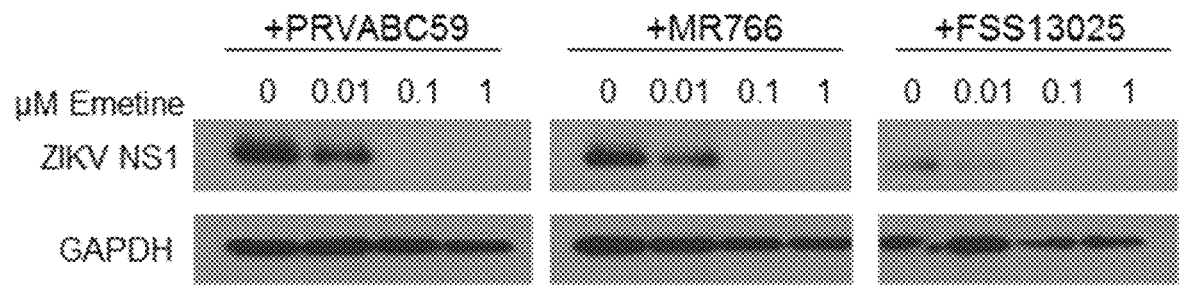
FIG. 3 shows Western blot analysis of intracellular ZIKV NS1 levels in SNB-19 cells.
Figure 4:
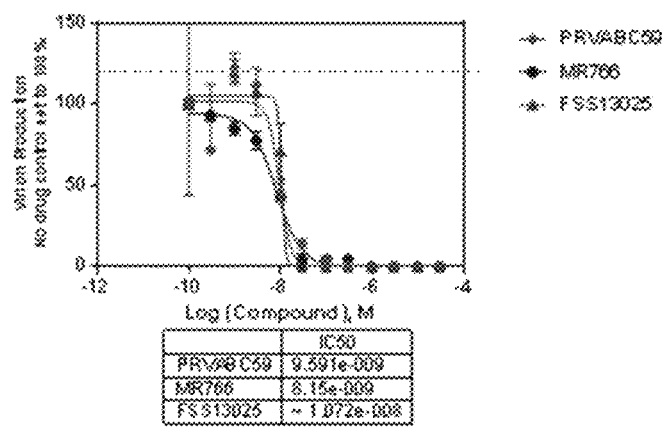
FIG. 4 shows that infectious ZIKV production is reduced for all three strains of ZIKV tested in SNB-19 cells. IC50 for each strain is ≤~10 nM. Emetine is effective against ZIKV infection when added before or after infection.
Figure 5:
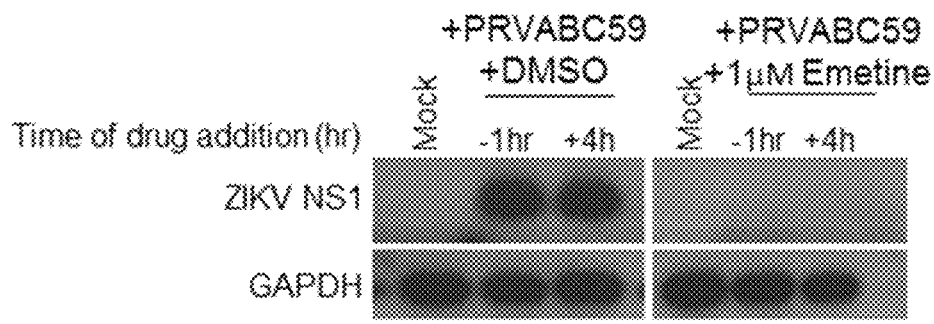
FIG. 5 shows Western blot analysis of ZIKV NS1 protein levels in SNB-19 cells after a 24-hour infection. Drug (emetine) was added at 1 µM either 1-hour prior to infection with PRVABC59-ZIKV, or 4-hours post infection with PRVABC59-ZIKV.
Figure 6A:
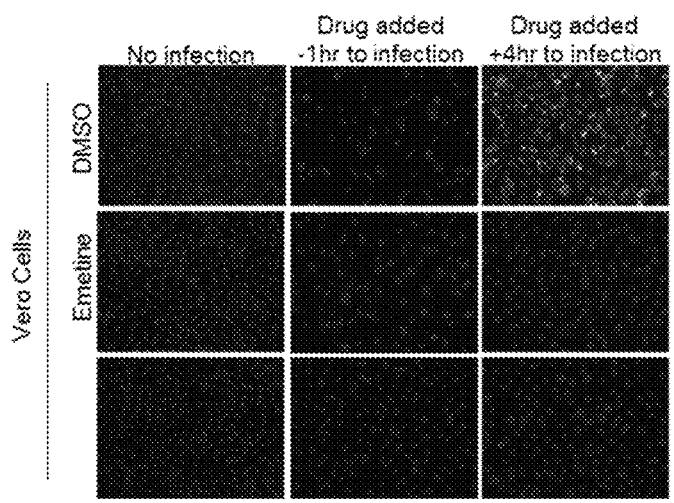
FIGS. 6A-B show IF staining of ZIKV-ENV Vero cells after a 24-hour infection. Drug was added at 1 µM either 1-hour prior to infection with PRVABC59-ZIKV, or 4-hours post infection with PRVABC59-ZIKV. Percentages of ZIKV-ENV+ cells are shown in FIG. 6B.
Figure 6B:
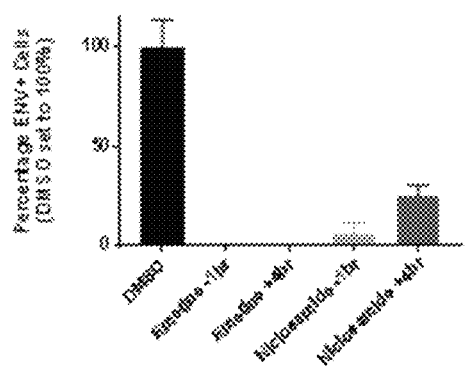

| Compound ID | Structure |
|---|---|
| HAL005-002 | 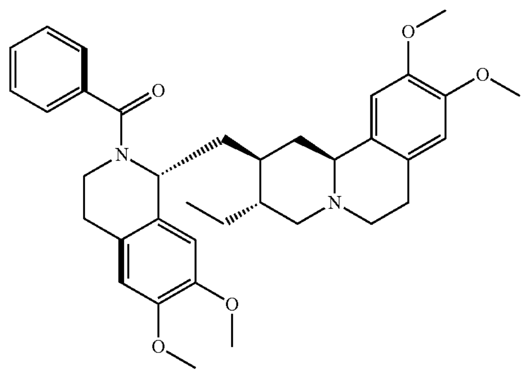 |
| HAL005-004 | 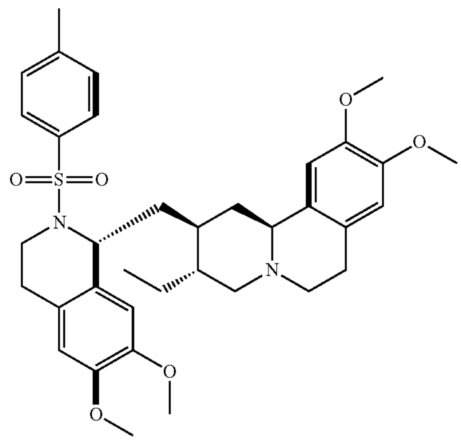 |
| HAL005-006 | 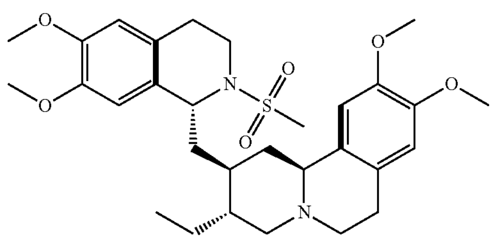 |
| KSH009-100 | 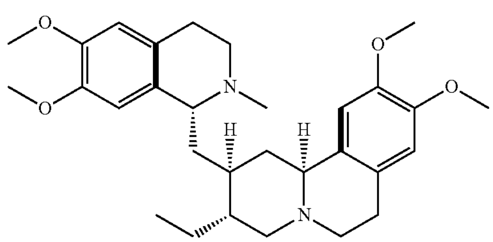 |
| KSH009-099 | 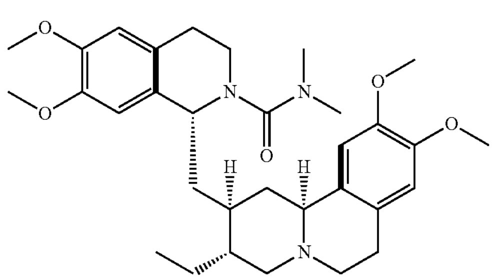 |

TABLE 1-continued

| Compound ID | Structure |
| --- | --- |
| KSH009-097 | 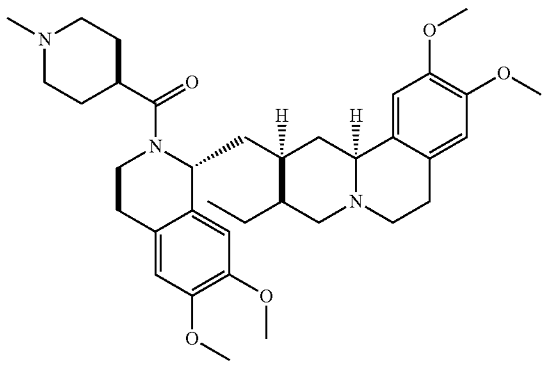 |
| KSH010-004 | 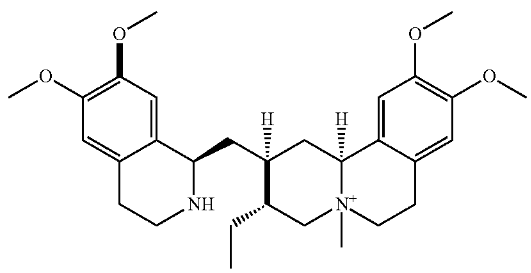 |
| KSH009-095 | 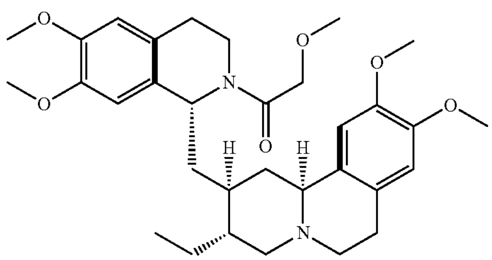 |
| HSK010-001 | 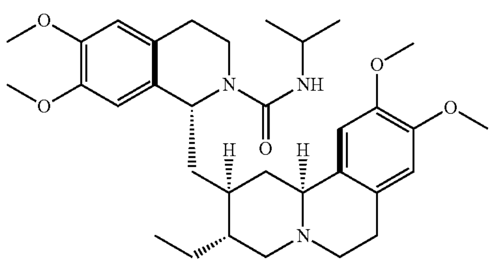 |
| kSH009-098 | 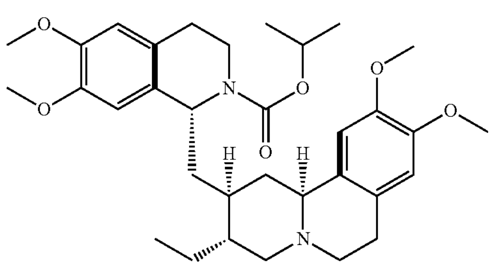 |

TABLE 1-continued

| Compound ID | Structure |
|---|---|
| KSH009-096 | (structure shown) |
| WWH012-070 | (structure shown) |

In some embodiments, the at least one emetine compound comprises a compound selected from among:
1. HAL005-002: (2S,3R,11bS)-3-ethyl-1,3,4,6,7,11b-hexahydro-9,10-dimethoxy-2-[[(1R)-1,3,4-trihydro-2-benzoyl-6,7-dimethoxy-1-isoquinolinyl]methyl]-2H-Benzo[a]quinolizine;
2. HAL005-004: (2S,3R,11bS)-3-ethyl-1,3,4,6,7,11b-hexahydro-9,10-dimethoxy-2-[[(1R)-1,3,4-trihydro-2-(4-methylbenzenesulfonyl)-6,7-dimethoxy-1-isoquinolinyl]methyl]-2H-Benzo[a]quinolizine;
3. HAL005-006: (2S,3R,11bS)-3-ethyl-1,3,4,6,7,11b-hexahydro-9,10-dimethoxy-2-[[(1R)-1,3,4-trihydro-2-methanesulfonyl-6,7-dimethoxy-1-isoquinolinyl]methyl]-2H-Benzo[a]quinolizine;
4. KSH009-100: (2S,3R,11bS)-3-ethyl-1,3,4,6,7,11b-hexahydro-9,10-dimethoxy-2-[[(1R)-1,3,4-trihydro-2-methyl-6,7-dimethoxy-1-isoquinolinyl]methyl]-2H-Benzo[a]quinolizine;
5. KSH009-099: (2S,3R,11bS)-3-ethyl-1,3,4,6,7,11b-hexahydro-9,10-dimethoxy-2-[[(1R)-1,3,4-trihydro-2-dimethylcarbamyl-6,7-dimethoxy-1-isoquinolinyl]methyl]-2H-Benzo[a]quinolizine;
6. KSH009-097: (2S,3R,11bS)-3-ethyl-1,3,4,6,7,11b-hexahydro-9,10-dimethoxy-2-[[(1R)-1,3,4-trihydro-2-(1-methylpiperidine-4-carbonyl)-6,7-dimethoxy-1-isoquinolinyl]methyl]-2H-Benzo[a]quinolizine;
7. KSH010-004: N-methylemetine ammonium salt;
8. KSH009-095: (2S,3R,11bS)-3-ethyl-1,3,4,6,7,11b-hexahydro-9,10-dimethoxy-2-[[(1R)-1,3,4-trihydro-2-methoxyacetyl-6,7-dimethoxy-1-isoquinolinyl]methyl]-2H-Benzo[a]quinolizine;
9. KSH010-001: (2S,3R,11bS)-3-ethyl-1,3,4,6,7,11b-hexahydro-9,10-dimethoxy-2-[[(1R)-1,3,4-trihydro-2-(1-metylethyl)carbamyl-6,7-dimethoxy-1-isoquinolinyl]methyl]-2H-Benzo[a]quinolizine;
10. KSH009-098: (2S,3R,11bS)-3-ethyl-1,3,4,6,7,11b-hexahydro-9,10-dimethoxy-2-[[(1R)-1,3,4-trihydro-2-(1-metylethoxy)carbonyl-6,7-dimethoxy-1-isoquinolinyl]methyl]-2H-Benzo[a]quinolizine;
11. KSH009-096: (2S,3R,11bS)-3-ethyl-1,3,4,6,7,11b-hexahydro-9,10-dimethoxy-2-[[(1R)-1,3,4-trihydro-2-(morpholine-4-carbonyl)-6,7-dimethoxy-1-isoquinolinyl]methyl]-2H-Benzo[a] quinolizine; and
12. WWHO12-070: (2S,3R,11bS)-3-ethyl-1,3,4,6,7,11b-hexahydro-9,10-dimethoxy-2-[[(1R)-1,3,4-trihydro-2-ethoxycarbonyl-6,7-dimethoxy-1-isoquinolinyl]methyl]-2H-Benzo[a]quinolizine;

or a prodrug, metabolite, or derivative thereof, or a pharmaceutically acceptable salt of any of the foregoing.

In some embodiments, the at least one emetine compound is emetine or an emetine derivative having the structure of Formula 1 or Formula 2:

Formula 1

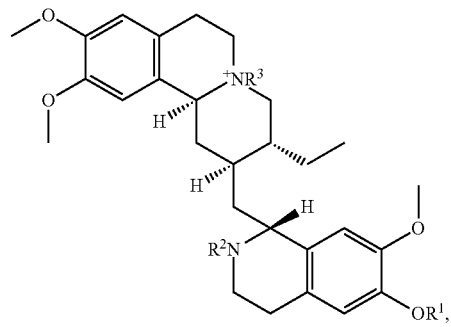

Formula 2

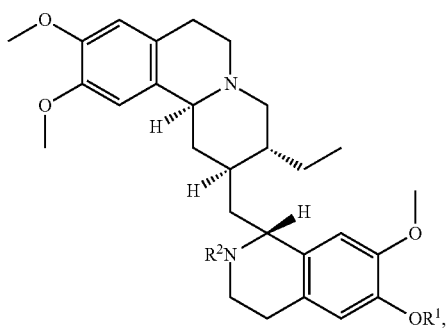

or a pharmaceutically acceptable salt of Formula 1 or Formula 2,
where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2R$ where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2NR'R"$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —P(O)OR'OR" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

In some embodiments, the at least one emetine compound does not comprise emetine.

In some embodiments, the at least one emetine compound comprises a combination of two or more of the emetine compounds.

Optionally, the at least one emetine compound may be administered with additional agents, such as other emetine compounds, or other agents. For example, the additional agent may be one or more agents useful for treating or preventing Flavivirus infection, or a symptom thereof. In some embodiments, the method further comprises administering an additional agent, wherein the at least one emetine compound and the additional agent are administered simultaneously, together within the same composition or in separate compositions. In other embodients, the at least one emetine compound and the additional agent are administered consecutively in any order. Thus, one or more additional agents may be administered within the same formulation as the at least one emetine compound, or in a separate formulation before, during, and/or after administration of the at least one emetine compound.

In some embodiments, the subject has the Flavivirus infection at the time of administration, and the at least one emetine compound is administered as therapy. Optionally, the method may further include, prior to administering the at least one emetine compound, identifying the subject as having the Flavivirus infection. Subjects may be identified, for example, by assaying a biological sample obtained from the subject for the presence of Flavivirus nucleic acids or Flavivirus proteins, using methods such as transcriptase-polymerase chain reaction (RT-PCR), immunological assay, or Plaque-reduction neutralization testing (PRNT).

In some embodiments, the subject does not have the Flavivirus infection at the time of said administering, and the at least one emetine compound is administered as prophylaxis.

In the therapeutic and prophylactic methods, at least one emetine compound may be administered by any effective route. In some embodiments, the at least one emetine compound is administered orally, nasally, rectally, parenterally, subcutaneously, intramuscularly, or intravascularly.

The at least one emetine compound may be administered within a composition that further includes a pharmaceutically acceptable buffer, carrier, or diluent.

Another aspect of the invention concerns a method for inhibiting Flavivirus infection in human or non-human animal cells in vitro or in vivo, said method comprising contacting an effective amount of at least one emetine compound to a human or non-human animal cell in vitro or in vivo before or after exposure of the cell to Flavivirus. The Flavivirus infection may be a Zika virus infection or other Flavivirus infection.

In some embodiments of the inhibition method, the at least one emetine compound comprises emetine, cephaeline, psychotrine, o-methyl psychotrine, or emetamine, or a prodrug, metabolite, or derivative of any of the foregoing, or a pharmaceutically acceptable salt of any of the foregoing. In some embodiments of the inhibition method, the at least one emetine compound is cephaeline, or a prodrug, metabolite, or derivative thereof, or a pharmaceutically acceptable salt of any of the foregoing. In some embodiments of the inhibition method, the emetine compound comprises cephaeline isoamyl ether or cephaeline ethyl ether, or a prodrug, metabolite, or derivative thereof, or a pharmaceutically acceptable salt of any of the foregoing. Cephaeline ethyl ether (KSH010-075) and cephaeline isoamyl ether can be synthesized, for example, by a Williamson etherification of cephaeline. In some embodiments of the inhibition method, the at least one emetine compound is dehydroemetine, or a prodrug, metabolite, or derivative thereof, or a pharmaceutically acceptable salt of any of the foregoing.

In some embodiments of the inhibition method, the at least one emetine compound comprises a compound in Table 1, or a prodrug, metabolite, or derivative thereof, or a pharmaceutically acceptable salt of any of the foregoing. In some embodiments of the inhibition method, the at least one emetine compound is emetine or an emetine derivative having the structure of Formula 1 or Formula 2:

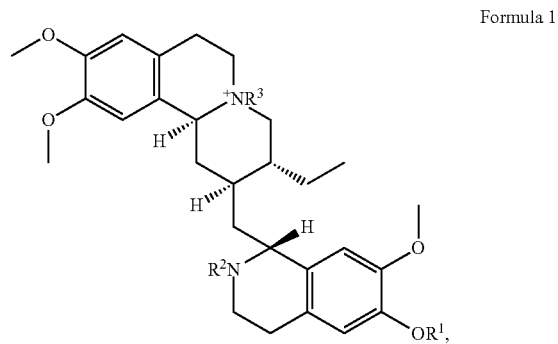

Formula 1

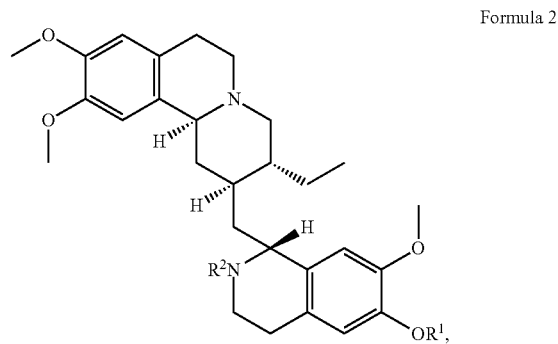

Formula 2 or a pharmaceutically acceptable salt of Formula 1 or Formula 2, where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2R$ where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2NR'R"$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —P(O)OR'OR" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

Emetine compounds disclosed herein, such as those in Table 1, can be prepared by amidation, alkylation, sulfamidation, urea formation, urethane formation, or quaternization of emetine, or carbonation of cephaeline by well established methods in the art.

In some embodiments of the inhibition method, the at least one emetine compound comprises a combination of two or more of the emetine compounds.

In some embodiments of the inhibition method, the at least one emetine compound does not comprise emetine.

In some embodiments of the inhibition method, the method further includes contacting the human or non-human animal cell in vitro or in vivo, with an additional agent, before or after exposure of the cell to Flavivirus, wherein the at least one emetine compound and the additional agent are administered simultaneously, together within the same composition or in separate compositions.

In some embodiments of the inhibition method, the method further includes contacting the human or non-human animal cell in vitro or in vivo with an additional agent, before or after exposure of the cell to Flavivirus, wherein the at least one emetine compound and the additional agent are administered consecutively in any order.

Another aspect of the invention concerns a composition comprising a combination of two or more emetine compounds. In some embodiments of the composition, the at least one emetine of the combination comprises emetine, cephaeline, psychotrine, o-methyl psychotrine, or emetamine, or a prodrug, metabolite, or derivative of any of the foregoing, or a pharmaceutically acceptable salt of any of the foregoing. In some embodiments of the composition, the at least one emetine compound of the combination comprises emetine, cephaeline, psychotrine, o-methyl psychotrine, emetamine, or a compound in Table 1, or a prodrug, metabolite, or derivative of any of the foregoing, or a pharmaceutically acceptable salt of any of the foregoing. In some embodiments of the composition, the at least one emetine compound is cephaeline, or a prodrug, metabolite, or derivative thereof, or a pharmaceutically acceptable salt of any of the foregoing. In some embodiments of the composition, the emetine compound comprises cephaeline isoamyl ether or cephaeline ethyl ether, or a prodrug, metabolite, or derivative thereof, or a pharmaceutically acceptable salt of any of the foregoing. In some embodiments of the composition, the at least one emetine compound is dehydroemetine, or a prodrug, metabolite, or derivative thereof, or a pharmaceutically acceptable salt of any of the foregoing.

In some embodiments of the composition, the at least one emetine compound of the combination is emetine or an emetine derivative having the structure of Formula 1 or Formula 2:

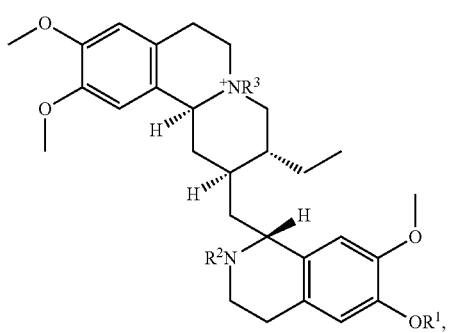

Formula 1

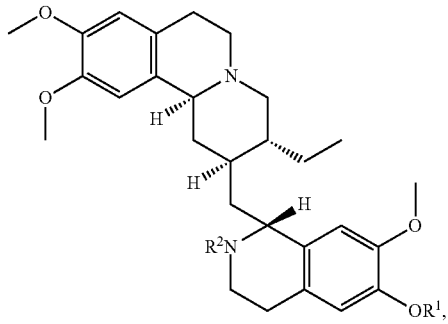

Formula 2 or a pharmaceutically acceptable salt of Formula 1 or Formula 2, where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2R$ where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2NR'R''$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$P(O)OR'OR''$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

In some embodiments of the composition, the combination does not comprise emetine.

Another aspect of the invention concerns a composition comprising at least one emetine compound; and an additional agent effective for the treatment of one or more symptoms of Flavivirus infection. In some embodiments of the composition, the at least one emetine compound comprises emetine, cephaeline, psychotrine, o-methyl psychotrine, or emetamine, a compound in Table 1, or a prodrug, metabolite, or derivative of any of the foregoing, or a pharmaceutically acceptable salt of any of the foregoing. In some embodiments of the composition, the emetine compound comprises cephaeline isoamyl ether or cephaeline ethyl ether, or a prodrug, metabolite, or derivative thereof, or a pharmaceutically acceptable salt of any of the foregoing. In some embodiments of the composition, the at least one emetine compound is dehydroemetine, or a prodrug, metabolite, or derivative thereof, or a pharmaceutically acceptable salt of any of the foregoing.

In some embodiments of the composition, the at least one emetine compound comprises emetine or an emetine derivative having the structure of Formula 1 or Formula 2:

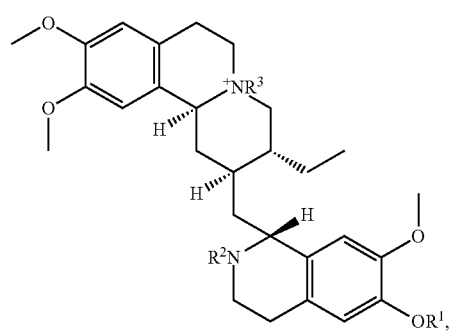

Formula 1

Formula 2

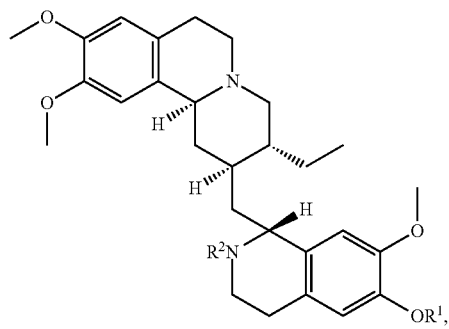

or a pharmaceutically acceptable salt of Formula 1 or Formula 2,
where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R",
where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2R$ where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2NR'R"$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —P(O)OR'OR" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

In some embodiments of the composition, the at least one emetine compound does not comprise emetine.

Derivatives of any of the emetine compounds can be synthesized by chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O(+)$, chlorination ($Cl_2$) bromination ($Br_2$), iodination ($I_2$), chlorohydrin formation ($Cl_2/H_2O$), bromohydrin formation ($Br_2/H_2O$), ether formation ($H^+$/ROH), oxymercuration ($Hg(OAc)_2/H_2O$), oxymercuration, ($Hg(OAc)_2$/ROH), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial reduction (Na/$NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hoffmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $SN^2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+others), protection as silyl ethers, thiol formation ($SN^2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R-X plus catalyst), Friedel Crafts acylation (RCOX plus catalyst), iodination ($I_2$/catalyst), Side chain oxidation ($KMnO_4$), reduction of nitro groups, reduction of aromatic ketones, Side chain bromination, nucleophilic aromatic substitution (SNAr), and aryne formation (SNAr via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation (ROHI/F), acetal hydrolysis ($H_3O^+$), imine, formation ($RNH_2$), Enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles ($P_2O_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines (LiAlH$_4$), hydrolysis to carboxylic acids. Optionally, potential derivatives of compounds disclosed herein can be tested for caspase activity and/or the ability to inhibit virally-induced apoptosis and/or suppress viral replication using methods disclosed herein (e.g., caspase 3/7 activity assay, ATP cell viability assay) or using other methods known in the art.

In some embodiments, the derivatives of emetine have a structure of Formula 1 or Formula 2, or a pharmaceutically acceptable salt thereof. In some embodiments, the emetine compound is a derivative or prodrug of emetine or cephaeline such as those disclosed in U.S. Patent Publication 2014/0148377 (Bakare O.), or U.S. Patent Publication 2017/0190700 (Bakare O. et al.), U.S. Patent Publication 20150210712 (Blumberg L C et al.), Lasslo A et al., "Chemical and Pharmacologic Studies on Emetine and Quaternary Emetine Derivatives," *Journal of Pharmaceutical Sciences*, January 1950, 39(1):43-46; Pyman F L et al., "The Action of Certain Emetine Derivatives on Amoebae," *Journal of Pharmacology and Experimental Therapeutics*, October 1917, 10(4):237-241, which are each incorporated by reference herein in their entireties.

In some embodiments of the methods, compositions, kits, and packaged dosage formulations of the invention, the Flavivirus infection is Zika virus, West Nile virus, dengue virus (e.g., type 1, 2, 3, or 4), tick-borne encephalitis virus, Japanese encephalitis virus, St. Louis encephalitis virus, or yellow fever virus. Other members of the genus can be found in Kuno G et al., *Journal of Virology*, 1998, "Phylogeny of the Genus Flavivirus," 72(1):73-83, which is incorporated herein by reference. In some embodiments, the Flavivirus is Zika virus. The Zika virus may be any origin or lineage (e.g., African, Asian, American, Brazilian). Examples of Zika virus strains include but are not limited to MR766 (1947 Uganda strain), FSS13025 (2010 Cambodian strain), PRVABC59 (2015 Puerto Rican strain), GZ01/2016 (2016 Chinese strain (ex Venezuela)), H/PF/2013 (2013 French Polynesian strain), IBH30656 (1968 Nigerian strain), Paraiba 2015 (2015 Brazilian strain), PLCal_ZV (2013 Canadian strain (ex Thailand)), SMGC-1 (2016 Chinese strain), SPH 2015 (2015 Brazilian strain), and SZ01 (2016 Chinese strain).

In each of the aforementioned methods compositions, kits, and dosage formulations, additional agents (i.e., in addition to the one or more emetine compounds) that may be administered to the subject, contacted with the cell, or included in the compositions. In some embodiments, the additional agent is useful for the treatment or prevention of Flavivirus infection, such as Zika virus infection. For example, an additional agent may be selected from among:
  (a) a niclosamide compound, or
  (b) an emricasan compound, or
  (c) a cyclin-dependent kinase (CDK) inhibitor, or
  (d) a proteasome inhibitor, or
  (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

The niclosamide compound may be: (a) niclosamide, (b) a niclosamide derivative, (c) a metabolite or prodrug of (a) or (b), or (d) a pharmaceutically acceptable salt of (a), (b), or (c). In some embodiments, the niclosamide or niclosamide derivative has a structure of Formula 3, Formula 4, Formula 5, or Formula 6.

In some embodiments, the niclosamide or niclosamide derivative has a structure of Formula 3:

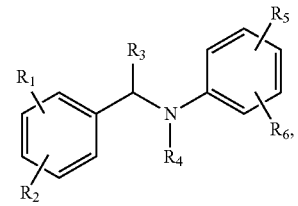

Formula 3 or a pharmaceutically acceptable salt thereof, where $R_1$, $R_2$, $R_3$, $R_4$, $R_5$, $R_6$ can be independently selected from the group consisting of a H; F; Cl; Br; I; OH; carbonyl (=O); (C$_{1-6}$)alkyl, such as methyl, ethyl, n-propyl, isopropyl, n-butyl, sec-butyl, isobutyl, tert-butyl; (C$_{2-6}$)alkenyl, such as ethenyl, propenyl, butenyl, where the double bond can be located at any position in the alkenyl carbon chain, including any alkenyl conformational isomers; (C$_{2-6}$)alkynyl, where the triple bond can be located at any position in the alkenyl carbon chain, including any alkynyl conformational isomers; ether [—OR, where R can include (C$_{1-6}$)alkyl, such as methyl, ethyl, n-propyl, isopropyl, n-butyl, sec-butyl, isobutyl, tert-butyl; and (C$_{2-6}$)alkenyl, such as ethenyl, propenyl, butenyl, where the double bond can be located at any position in the alkenyl carbon chain, including any alkenyl conformational isomers]; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X can include F, Cl, Br, and I]; carbonyl [—COR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aldehyde (—CHO); ester [—OC(=O)R, —ROC(=O)R', RC(=O)OR', —C(=O)OR', where R and R' can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers]; carbonate ester [—OCOOR, where R can include $(C_{1-6})$alkyl, such as methyl, ethyl, n-propyl, isopropyl, n-butyl, sec-butyl, isobutyl, tert-butyl; and $(C_{1-6})$alkenyl, such as ethenyl, propenyl, butenyl, where the double bond can be located at any position in the alkenyl carbon chain, including any alkenyl conformational isomers]; carboxyl (—COOH); amide [—CONR'R", where R' and R" can be independently selected from hydrogen; alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, including any alkenyl conformational isomers]; amines [—NR'R", where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R"), where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; borinate [—B(R')(OR"), where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosphino [—PR$_2$, where R can include hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosphate [—OP(=O)(OR)$_2$, where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers; phosphono [—RP(=O)(OH), where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; thiol (—SH); thioalkyl; alkylthio; sulfide [—SR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; disulfide [—SSR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers], sulfonamide; sulfinyl [—S(=O)R, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; sulfino (—SO$_2$H); sulfo (—SO$_3$H); thiocyanate; isothiocyanate; carbonothioyl [—C(=S)R where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers];

where $R_2$ and $R_4$ can be bonded together to form an $(C_{1-8})$ alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring; and where $R_4$ and $R_6$ can be bonded together to form an $(C_{1-8})$ alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring.

In some embodiments, the niclosamide or niclosamide derivative has the structure of Formula 4:

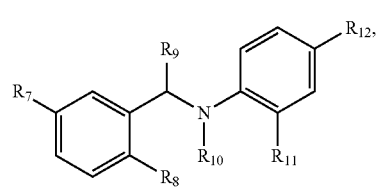

Formula 4 or a pharmaceutically acceptable salt thereof, where $R_7$, $R_8$, $R_9$, $R_{10}$, $R_{11}$, $R_{12}$ can be independently selected from the group consisting of a H; F; Cl; Br; I; OH; carbonyl (=O); $(C_{1-6})$alkyl, such as methyl, ethyl, n-propyl, isopropyl, n-butyl, sec-butyl, isobutyl, tert-butyl; $(C_{2-6})$alkenyl, such as ethenyl, propenyl, butenyl, where the double bond can be located at any position in the alkenyl carbon chain, including any alkenyl conformational isomers; $(C_{2-6})$alkynyl, where the triple bond can be located at any position in the alkenyl carbon chain, including any alkynyl conformational isomers; ether [—OR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X can include F, Cl, Br, and I]; carbonyl [—COR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aldehyde (—CHO); ester [—OC(=O)R, —ROC(=O)R', RC(=O)OR', —C(=O)OR', where R and R' can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers]; carbonate ester [—OCOOR, where R can include $(C_{1-6})$alkyl, such as methyl, ethyl, n-propyl, isopropyl, n-butyl, sec-butyl, isobutyl, tert-butyl; and $(C_{1-6})$alkenyl, such as ethenyl, propenyl, butenyl, where the double bond can be located at any position in the alkenyl carbon chain, including any alkenyl conformational isomers]; carboxyl (—COOH); amide [—CONR'R", where R' and R" can be independently selected from hydrogen; alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, including any alkenyl conformational isomers]; amines [—NR'R", where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R")], where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; borinate [—B(R')(OR")], where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosophino [—PR$_2$, where R can include hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosphate [—OP(=O)(OR)$_2$, where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers; phosphono [—RP(=O)(OH), where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; thiol (—SH); thioalkyl; alkylthio; sulfide [—SR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; disulfide [—SSR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers], sulfonamide; sulfinyl [—S(=O)R, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; sulfino (—SO$_2$H); sulfo (—SO$_3$H); thiocyanate; isothiocyanate; carbonothioyl [—C(=S)R where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers];

where $R_7$ and $R_{10}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring;

where $R_8$ and $R_{10}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring; and where $R_{10}$ and $R_{11}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring.

In some embodiments, the niclosamide or niclosamide derivative has the structure of Formula 5:

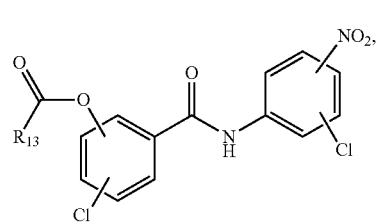

Formula 5 or a pharmaceutically acceptable salt thereof, where $R_{13}$ can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers.

In some embodiments, the niclosamide or niclosamide derivative has the structure of Formula 6:

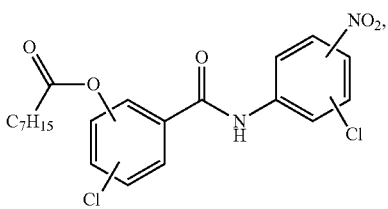

Formula 6 or a pharmaceutically acceptable salt thereof.

In some embodiments, the additional compound is a derivative of niclosamide such as p-niclosamide, which is incorporated herein by reference in its entirety, or an acyl derivative of niclosamide, such as DK-520, which is incorporated herein by reference in its entirety, or a pharmaceutically acceptable salt thereof.

The emricasan compound may comprise: (a) emricasan, (b) an emricasan derivative, (c) a metabolite or prodrug of (a) or (b), or (d) a pharmaceutically acceptable salt of (a), (b), or (c). In some embodiments, the emricasan or emricasan derivative has the structure of Formula 7:

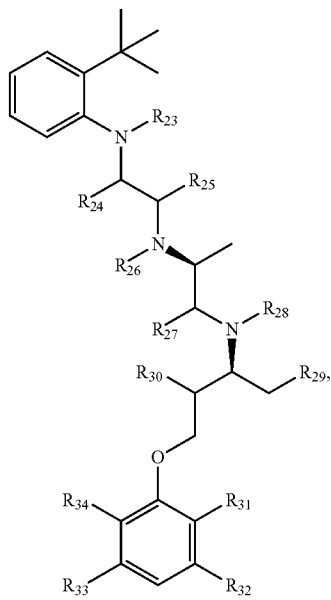

Formula 7 or a pharmaceutically acceptable salt thereof, where $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$, can be independently selected from the group consisting of: H; F; Cl; Br; I; OH; carbonyl (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers;
where $R_{23}$ and $R_{24}$ can be bonded together to form an $(C_{2-8})$alkane ring and/or $(C_{2-8})$alkene ring, such as a five-membered ring or a six-membered ring; where $R_{23}$ and $R_{25}$ can be bonded together to form an $(C_{2-8})$alkane ring and/or $(C_{2-8})$alkene ring, such as a five-membered ring or a six-membered ring, where $R_{24}$ and $R_{26}$ can be bonded together to form an $(C_{2-8})$alkane ring and/or $(C_{2-8})$alkene ring, such as a five-membered ring or a six-membered ring; where $R_{27}$ and $R_{30}$ can be bonded together to form an $(C_{2-8})$alkane ring and/or $(C_{2-8})$alkene ring, such as a five-membered ring or a six-membered ring; where $R_{28}$ and $R_{29}$ can be bonded together to form an $(C_{2-8})$alkane ring and/or $(C_{2-8})$alkene ring, such as a five-membered ring or a six-membered ring; where $R_{27}$ and $R_{30}$ can be bonded together to form an $(C_{2-8})$alkane ring and/or $(C_{2-8})$alkene ring, such as a five-membered ring or a six-membered ring; and where $R_{29}$ and $R_{30}$ can be bonded together to form an $(C_{2-8})$alkane ring and/or $(C_{2-8})$alkene ring, such as a five-membered ring or a six-membered ring.

In some embodiments, the additional agent comprises a CDK inhibitor, and the CDK inhibitor has a structure of Formula 8 (PHA-690509 or a derivative thereof), Formula 9 (Alvocidib or a derivative thereof), Formula 10 (PHA-793887 or a derivative thereof), Formula 11 (Dinaciclib or a derivative thereof), or Formula 12 (Seliciclib or a derivative thereof), or a pharmaceutically acceptable salt of any of the foregoing.

In some embodiments, the CDK inhibitor has the structure of Formula 8, which encompasses the CDK inhibitor PHA-690509 and derivatives of PHA-690509:

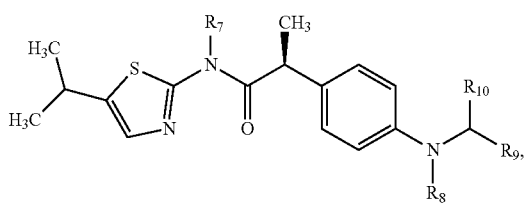

Formula 8 or a pharmaceutically acceptable salt thereof,
where $R_7$, $R_8$, $R_9$, $R_{10}$ can be independently selected from the group consisting of H; F; Cl; Br; I; OH; carbonyl (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocyanate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; and $(C_{2-4})$alkenyl, such as ethenyl, propenyl, butenyl, where the double bond can be located at any position in the alkenyl carbon chain, and including any alkenyl conformational isomers; and where $R_8$ and $R_9$ can be bonded together to form a $(C_{2-8})$lactam ring with or without a double carbon-carbon bond.

In some embodiments, the CDK inhibitor has the structure shown in Formula 9, encompassing the CDK inhibitor Alvocidib and derivatives of Alvocidib:

Formula 9

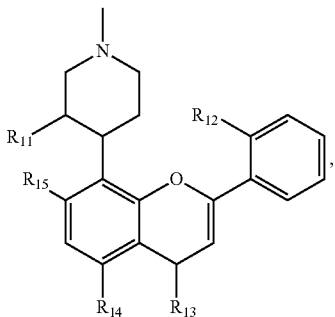

or a pharmaceutically acceptable salt thereof,
where $R_{11}$, $R_{12}$, $R_{13}$, $R_{14}$ and $R_{15}$ can be independently selected from a group consisting of H; F; Cl; Br; I; OH; carbonyl (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; where $R_{11}$ and $R_{15}$ can be bonded together to form an $(C_{2-8})$alkane ring and/or $(C_{2-8})$alkene ring, such as a five-membered ring or a six-membered ring; and where $R_{13}$ and $R_{14}$ can be bonded together to form an $(C_{2-8})$alkane ring and/or $(C_{2-8})$alkene ring, such as a five-membered ring or a six-membered ring.

In some embodiments, the CDK inhibitor has the structure Formula 10, which encompasses the CDK inhibitor PHA-793887 and derivatives of PHA-793887:

Formula 10

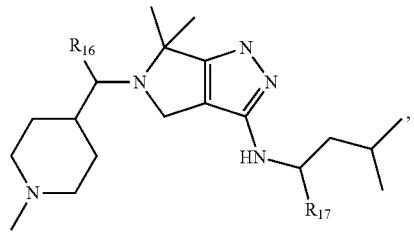

or a pharmaceutically acceptable salt thereof, where $R_{16}$ and $R_{17}$ can be independently selected from a group consisting of H; F; Cl; Br; I; OH; carbonyl (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX);

carbonyl [—COR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; sulfinyl [—S(=O)R, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; (C$_{1-4}$)alkyl, such as methyl, ethyl, n-propyl, isopropyl, n-butyl, sec-butyl, isobutyl, tert-butyl; and (C$_{2-4}$)alkenyl, such as ethenyl, propenyl, butenyl, where the double bond can be located at any position in the alkenyl carbon chain, and including any alkenyl conformational isomers.

In some embodiments, the CDK inhibitor has the structure of Formula 11, which encompasses the CDK inhibitor Dinaciclib and derivatives of Dinaciclib:

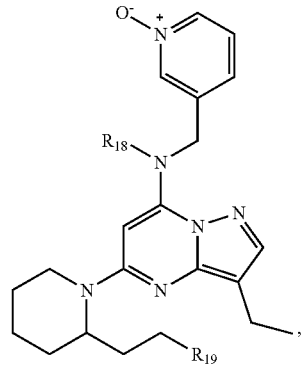

Formula 11

Formula 11, or a pharmaceutically acceptable salt thereof, where R$_{18}$ and R$_{19}$ can be selected from the group consisting of H; F; Cl; Br; I; OH; carbonyl (=O); ether [—OR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; cyanate (—OCN); isocyanate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; and $(C_{2-4})$alkenyl, such as ethenyl, propenyl, butenyl, where the double bond can be located at any position in the alkenyl carbon chain, and including any alkenyl conformational isomers.

In some embodiments, the CDK inhibitor has the structure of Formula 12, which encompasses the CDK inhibitor Selicicib and derivatives of Selicicib:

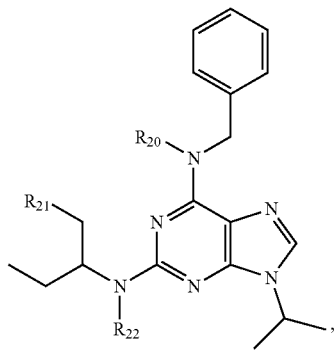

Formula 12 or a pharmaceutically acceptable salt thereof, where $R_{20}$, $R_{21}$, $R_{22}$ can be selected from the group consisting of H; F; Cl; Br; I; OH; carbonyl (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; and $(C_{2-4})$alkenyl, such as ethenyl, propenyl, butenyl, where the double bond can be located at any position in the alkenyl carbon chain, and including any alkenyl conformational isomers.

In some embodiments, the additional agent is a CDK inhibitor selected from among Alvocidib, Kenpaullone, Olomoucine, Purvalanol A, Purvalanol B, Seliciclib, NU-6027, Indirubin, Flavopiridol, AT7519, PD-0332991, SNS-032, PHA-793887, PHA-690509, RGB-286147, BS-194, BS-181, AZD-5438, R-547, Dinaciclib, Milciclib, BMS-265246, 7-Hydroxystaurosporine, CGP-60474, CDK9 inhibitor, NU-6102, Fascaplysin, Cdk4/6 Inhibitor IV, or a prodrug, metabolite, derivative, or pharmaceutically acceptable salt of any of the foregoing.

In some embodiments, the additional compound is selected from among SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Dinaciclib, Vincristine, Idarubicin, Thapsigargin, Lexibulin, Ixazomib, Cephalomannine, Mitoxantrone, MLN-2238, Demecolcine, RGB-286147, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, 7-Hydroxystaurosporine, CGP-60474, Floxuridine, Go-6976, OSU-03012, a prodrug of any of the foregoing, a metabolite of any of the foregoing, a derivative of any of the foregoing, or a pharmaceutically acceptable salt of any of the foregoing.

In some embodiments of the methods, compositions, kits, and packaged dosage formulations of the invention, two or more compounds useful for treating or preventing Zika virus or other Flavivirus infection by distinct mechanisms of action from one another may be utilized. For example, emetine compounds of the invention can inhibit or reduce Zika virus or other Flavivirus replication (e.g., Zika virus infection), and thus represent one class of compounds of the invention. Emricasan compounds are pan-caspase inhibitors, which inhibit Flavivirus-induced increase in caspase-3 activity, and reduce cell death, and represent another class of compounds of the invention. A combination of emetine compounds with emricasan or other emricasan compounds may exhibit a synergistic effect in protecting neural cells from Flavivirus-induced (e.g., Zika virus-induced) cell death.

The methods of the invention may be used to treat an existing Flavivirus infection in a subject, or the methods of the invention may be used prophylactically to prevent a Flavivirus infection in a subject. As used herein, in this context, the term "prevent" or "prevention" is inclusive of delaying the onset of infection and/or one or more symptoms of infection, and precluding the occurrence or reoccurrence of infection and/or one or more symptoms of infection.

Thus, in some embodiments, the subject has the Flavivirus infection at the time the at least one compound is administered, and the at least one compound is administered as therapy.

In some embodiments, the methods further comprise, prior to administering the at least one compound to the subject, identifying the subject as having the Flavivirus infection. The identifying step may comprise assaying a biological sample (e.g., blood, saliva, or urine) obtained from the subject for the presence of Flavivirus nucleic acids or Flavivirus proteins (e.g., Zika virus nucleic acids or Zika virus proteins). In some embodiments, assaying includes the use of reverse transcriptase-polymerase chain reaction (RT-PCR), immunological assay (e.g., ELISA), or Plaque-reduction neutralization testing (PRNT).

One or more compounds of the invention (also referred to herein as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the subject. In some embodiments, at least one compound of the invention is administered orally, nasally, rectally, parenterally, subcutaneously, intramuscularly, or intravascularly (e.g., intravenously).

Another aspect of the invention concerns a packaged dosage formulation comprising at least one compound emetine compound in a pharmaceutically acceptable dosage in one or more packages, packets, or containers.

Another aspect of the invention concerns a kit comprising, in one or more containers, at least one emetine compound.

In some embodiments, the kit comprises a combination of two or more emetine compounds. In some embodiments, the kit further comprises an additional agent effective for the treatment or prevention of Flavivirus virus infection. In some embodiments, the kit further comprises an additional agent effective for the treatment of one or more symptoms of Flavivirus infection.

Various techniques may be used to increase bioavailability of the emetine compounds of the invention Prodrugs employ various physical and chemical modifications to improve features of the active drug, and in some embodiments may be viewed as pharmacologically inactive prodrug functional groups that undergo a chemical transformation or enzymatic cleavage to liberate the active parent drug and produce the desired effect in the body. Utilizing a prodrug approach can yield benefits such as enhanced solubility, improved selective targeting of drugs to anatomical sites, protection from rapid metabolism and elimination, reduction toxic effects of an active drug on other parts of the body, and enhanced patient compliance.

Non-limiting examples of techniques useful for enhancing the bioavailability of BCS Class II drugs include use of co-solvents, hydrotropy, micronization, change in dielectric constant of solvent, amorphous forms, chemical modification of the drug, use of surfactants, inclusion complex, alteration of pH of solvent, use of hydrates or solvates, use of soluble prodrugs, application of ultrasonic waves, functional polymer technology, controlled precipitation technology, evaporative precipitation in aqueous solution, use of precipitation inhibitors, solvent deposition, precipitation, selective adsorption on insoluble carriers, size reduction technologies, lipid based delivery systems, micellar technologies, porous micro particle technology, solid dispersion technique, and various types of solid dispersion systems.

Other methods for enhancement of bioavailability (e.g., by enhancement of solubility) are described in Reddy M S et al., "Solubility enhancement of fenofibrate, a BCS class II drug, by self emulsifying drug delivery systems," *International Research Journal of Pharmacy*, 2011, 2(11): 173-177; Khamkar G S, "Self micro emulsifying drug delivery system (SMEED) o/w microemulsion for BCS Class II drugs: an approach to enhance oral bioavailability," *International Journal of Pharmacy and Pharmaceutical Sciences*, 2011, 3(3):1-3; Elgart A et al., "Improved oral bioavailability of BCS class 2 compounds by self nano-emulsifying drug delivery systems (SNEDDS): the underlying mechanisms for amiodarone and talinolol", *Pharm Res.*, 2013 December; 30(12):3029-44; Singh N. et al. "Techniques for bioavailability enhancement of BCS class II drugs: a review," *International Journal of Pharmaceutical and Chemical Science*, 2013, 2(2):1092-1101; Elkihel L et al., "Synthesis and orally macrofilaricidal evaluation of niclosamide lymphotropic prodrugs," Arzneimittelforschung, 1994, 44(11): 1259-64; and Kansara H. et al., "Techniques used to enhance bioavailability of BCS class II drugs: a review," *Int. J. Drug Dev. & Res.*, 2015, 7(1):82-93, which are each incorporated herein by reference in its entirety.

International Patent Publication WO 2016/004166 (Wang G et al.), which is incorporated herein by reference in its entirety, describes boron-based prodrugs of phenol- or aromatic hydroxyl group-containing therapeutic molecules, including niclosamide (Table 1, page 15). The boron-prodrug platform can be utilized to make prodrugs of compounds disclosed herein.

International Patent Publication WO 2009/143297 (Naweed Muhammad et al.), which is incorporated herein by reference in its entirety, describes carbonate prodrugs which comprise a carbonic phosphoric anhydride prodrug moiety attached to the hydroxyl or carboxyl group of a parent drug moiety.

Chemical reactions, reactants, and reagents that may be utilized to enhance solubility and make prodrugs of compounds are described in *March's Advanced Organic Chemistry*, 7$^{th}$ edition, 2013, Michael B. Smith, which is incorporated herein by reference in its entirety.

Compounds, and compositions comprising them, useful in the methods of the subject invention can be formulated according to known methods for preparing pharmaceutically useful compositions. Formulations are described in detail in a number of sources which are well known and readily available to those skilled in the art. For example, *Remington's Pharmaceutical Science* by E.W. Martin describes formulations which can be used in connection with the subject invention. In general, the compositions of the subject invention will be formulated such that an effective amount of at least one compound of the invention is combined with a suitable carrier or diluent in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the compounds of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide or polynucleotide based on the weight of the total composition including carrier or diluent.

The compounds of the subject invention can also be administered utilizing liposome technology, slow release capsules, implantable pumps, and biodegradable containers. These delivery methods can, advantageously, provide a uniform dosage over an extended period of time.

The compounds of the invention can also be modified by the addition of chemical groups, such as PEG (polyethylene glycol). PEGylated compounds can exhibit extended half-lives in vivo in comparison to compounds that are not PEGylated when administered in vivo. Compounds can also be modified to improve cell membrane permeability. In one embodiment, cell membrane permeability can be improved by attaching a lipophilic moiety, such as a steroid, to the compound. In another embodiment, compounds of the invention can be coupled to a cell-penetrating peptide (CPP). CPPs are typically short peptides that are highly cationic and typically include several arginine and/or lysine amino acids. CPPs can be classified as hydrophilic, amphiphilic, or periodic sequence.

The subject invention also concerns a packaged dosage formulation comprising in one or more containers at least compound, and/or composition of the subject invention formulated in a pharmaceutically acceptable dosage. The package can contain discrete quantities of the dosage formulation, such as tablet, capsules, lozenge, and powders. The quantity of compound in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

Optionally, the methods include, prior to administration of at least one compound of the invention, or re-administration of at least one compound of the invention, determining whether the subject has a Flavivirus infection (e.g., a Zika virus infection) or one or more symptoms consistent with a Flavivirus infection. In the case of Zika virus, during the first week after onset of symptoms, viral RNA can often be identified in serum; thus, Zika virus disease can be diagnosed by performing reverse transcriptase-polymerase chain reaction (RT-PCR) on serum. Urine and saliva samples may also be used for detection of Zika virus (Gourinat A-C et al. (2015) *Emerg Infect Dis*, vol. 21, no. 1, pp. 84-86; and Musso D et al. (2015) *J Clin Virol*, vol. 68, pp. 53-55).

Virus-specific IgM and neutralizing antibodies typically develop toward the end of the first week of illness; cross-reaction with related flaviviruses (e.g., dengue and yellow fever viruses) is common and may be difficult to discern. Plaque-reduction neutralization testing (PRNT) can be performed to measure virus-specific neutralizing antibodies and discriminate between cross-reacting antibodies in primary flavivirus infections.

In the case of Zika virus, some infected individuals will not know they have the disease because they will not have symptoms. The most common symptoms of Zika virus infection are fever, maculo-papular rash (often spreading from face to body), joint pain, retro-orbital pain, or conjunctivitis (red eyes). Other common symptoms include general non-specific such as myalgia, asthenia, and headache. The incubation period (the time from exposure to symptoms) for Zika virus disease is not known, but is likely to be a few days to a week. The illness is usually mild with symptoms lasting for several days to a week after being bitten by an infected mosquito. The Zika virus usually remains in the blood of an infected person for approximately a week but it can be found longer in some individuals.

Treatment methods optionally include steps of advising that the subject get plenty of rest and drink fluids for hydration and administration of agents that alleviate symptoms of Flavivirus infection (e.g., Zika virus infection), such as those that reduce fever and pain (e.g., acetaminophen and/or paracetamol). The methods may include administration of the fluids to the subject for hydration.

The subject may be any age or gender. In some embodiments, the subject is male. In some embodiments, the subject is female. In some embodiments, the subject is a post-pubescent female. In some embodiments, the subject is a post-pubescent, pre-menopausal female. In some embodiments, the subject is a non-pregnant female. In some embodiments, the subject is a pregnant female. In some embodiments, the subject has Guillain-Barré syndrome or another condition that is associated with ZIKV infection.

The invention further provides kits, including at least one emetine compound of the invention and pharmaceutical formulations, packaged into suitable packaging material, optionally in combination with instructions for using the kit components, e.g., instructions for performing a method of the invention. In one embodiment, a kit includes an amount of at least one emetine compound of the invention, and instructions for administering at least one emetine compound of the invention to a subject in need of treatment on a label or packaging insert. In further embodiments, a kit includes an article of manufacture, for delivering at least one compound of the invention into a subject locally, regionally or systemically, for example.

As used herein, the term "packaging material" refers to a physical structure housing the components of the kit. The packaging material can maintain the components in a sterile state, and can be made of material commonly used for such purposes (e.g., paper, corrugated fiber, glass, plastic, foil, ampules, etc.). The label or packaging insert can include appropriate printed and/or digital instructions, for example, for practicing a method of the invention, e.g., treating a Flavivirus infection (e.g., Zika virus infection), an assay for identifying a subject having a Flavivirus infection (e.g., Zika virus infection), etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a Flavivirus infection (e.g., Zika virus infection). Instructions may additionally include indications of a satisfactory clinical endpoint or any adverse symptoms that may occur, storage information, expiration date, or any information required by regulatory agencies such as the Food and Drug Administration or European Medicines Agency for use in a human subject.

The instructions may be digital or on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing at least one compound of the invention. The kit can also include components for assaying for the presence of Zika virus or other Flavivirus, e.g., an antibody or antibody fragment specific for a Zika virus or other Flavivirus antigen, one or more primers specific for Zika virus or other Flavivirus nucleic acids, a control sample or a standard. Each component of the kit can be enclosed within an individual container or in a mixture and all of the various containers can be within single or multiple packages.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compounds for treating or preventing Zika virus or other Flavivirus infection. Non-limiting examples of such materials include, but not limited to, buffers, diluents, carrier, package, container, vial and/or tube labels listing contents and/or instructions for use, and package inserts with instructions for use.

A label can be on or associated with a container containing a compound of the invention. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the compound(s) of the invention can be presented in a pack or dispenser device which can contain one or more unit dosage forms containing a compound disclosed herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Additional emetine compounds can be identified by determining whether the candidate compounds reduce virally-induced apoptosis and/or suppress viral replication.

Exemplified Embodiments

Examples of claimed embodiments of the invention include, but are not limited to:

Embodiment 1. A method for treating or preventing Flavivirus infection in a human or non-human animal subject, said method comprising administering an effective amount of at least one emetine compound to a subject in need thereof.

Embodiment 2. The method of embodiment 1, wherein the Flavivirus infection is Zika virus infection.

Embodiment 3. The method of embodiment 1 or 2, wherein the at least one emetine compound comprises emetine, cephaeline, psychotrine, o-methyl psychotrine, emetamine, cephaeline isoamyl ether, cephaeline ethyl ether, dehydroemetine, or a prodrug, metabolite, or derivative of any of the foregoing, or a pharmaceutically acceptable salt of any of the foregoing.

Embodiment 4. The method of one of embodiments 1 to 3, wherein the at least one emetine compound comprises a compound in Table 1, or a prodrug, metabolite, or derivative thereof, or a pharmaceutically acceptable salt of any of the foregoing.

Embodiment 5. The method of any preceding embodiment, wherein the emetine compound is emetine or an emetine derivative having the structure of Formula 1 or Formula 2:

Formula 1

Formula 2 or a pharmaceutically acceptable salt of Formula 1 or Formula 2, where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2R$ where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2NR'R''$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$P(O)OR'OR''$ where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

Embodiment 6. The method of any preceding embodiment, wherein the at least one emetine compound does not comprise emetine.

Embodiment 7. The method of any preceding embodiment, wherein the at least one emetine compound comprises a combination of two or more of the emetine compounds.

Embodiment 8. The method of any preceding embodiment, further comprising administering an additional agent, wherein the at least one emetine compound and the additional agent are administered simultaneously, together within the same composition or in separate compositions.

Embodiment 9. The method of any one of embodiments 1 to 8, further comprising administering an additional agent, wherein the at least one emetine compound and the additional agent are administered consecutively in any order.

Embodiment 10. The method of any preceding embodiment, wherein the subject has the Flavivirus infection at the time of said administering, and the at least one emetine compound is administered as therapy.

Embodiment 11. The method of embodiment 10, further comprising, prior to said administering, identifying the subject as having the Flavivirus infection.

Embodiment 12. The method of embodiment 11, wherein said identifying comprises assaying a biological sample obtained from the subject for the presence of Flavivirus nucleic acids or Flavivirus proteins.

Embodiment 13. The method of embodiment 12, wherein said assaying comprises use of reverse transcriptase-polymerase chain reaction (RT-PCR), immunological assay, or Plaque-reduction neutralization testing (PRNT).

Embodiment 14. The method of any one of embodiments 1 to 10, wherein the subject does not have the Flavivirus infection at the time of said administering, and the at least one emetine compound is administered as prophylaxis.

Embodiment 15. The method of any preceding embodiment, wherein the at least one compound is administered orally, nasally, rectally, parenterally, subcutaneously, intramuscularly, or intravascularly.

Embodiment 16. The method of any preceding embodiment, further comprising administering an additional agent for treating or preventing Flavivirus infection, or a symptom thereof, in the same formulation as the at least one emetine compound, or in a separate formulation before, during, or after administration of the at least one emetine compound.

Embodiment 17. The method of any preceding embodiment, wherein said administering comprises administering a composition to the subject, wherein the composition comprises the at least one emetine compound and a pharmaceutically acceptable buffer, carrier, or diluent.

Embodiment 18. A method for inhibiting Flavivirus infection in human or non-human animal cells in vitro or in vivo, said method comprising contacting an effective amount of at least one emetine compound to a human or non-human animal cell in vitro or in vivo before or after exposure of the cell to Flavivirus.

Embodiment 19. The method of embodiment 18, wherein the Flavivirus infection is Zika virus infection.

Embodiment 20. The method of embodiment 18 or 19, wherein the at least one emetine compound comprises emetine, cephaeline, psychotrine, o-methyl psychotrine, emetamine, cephaeline isoamyl ether, cephaeline ethyl ether, dehydroemetine, or a prodrug, metabolite, or derivative of any of the foregoing, or a pharmaceutically acceptable salt of any of the foregoing.

Embodiment 21. The method of embodiment 18 or 19, wherein the at least one emetine compound comprises a compound in Table 1, or a prodrug, metabolite, or derivative thereof, or a pharmaceutically acceptable salt of any of the foregoing.

Embodiment 22. The method of embodiment 1 or 2, wherein the at least one emetine compound comprises emetine or an emetine derivative having the structure of Formula 1 or Formula 2:

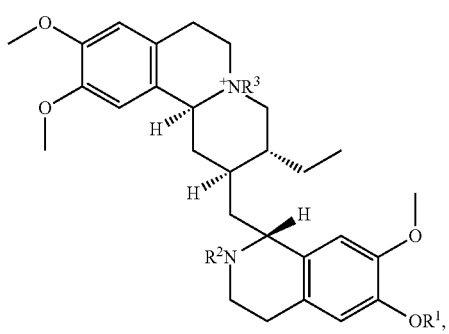

Formula 1

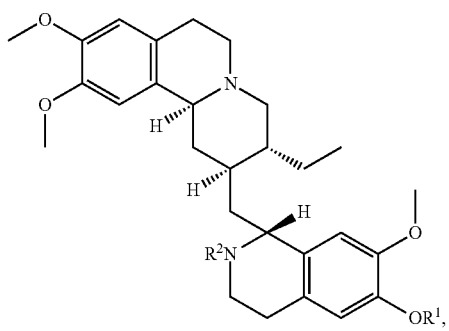

Formula 2 or a pharmaceutically acceptable salt of Formula 1 or Formula 2, where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2$R where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2$NR'R" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —P(O)OR'OR" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

Embodiment 23. The method of any preceding embodiment, wherein the at least one emetine compound comprises a combination of two or more of the emetine compounds.

Embodiment 24. The method of any preceding embodiment, wherein the at least one emetine compound does not comprise emetine.

Embodiment 25. The method of any preceding embodiment, further comprising contacting the human or non-human animal cell in vitro or in vivo, with an additional agent, before or after exposure of the cell to Flavivirus, wherein the at least one emetine compound and the additional agent are administered simultaneously, together within the same composition or in separate compositions.

Embodiment 26. The method of any one of embodiments 1 to 8, further comprising contacting the human or non-human animal cell in vitro or in vivo with an additional agent, before or after exposure of the cell to Flavivirus, wherein the at least one emetine compound and the additional agent are administered consecutively in any order.

Embodiment 27. A composition comprising a combination of two or more emetine compounds.

Embodiment 28. The composition of embodiment 27, wherein at least one emetine of the combination comprises emetine, cephaeline, psychotrine, o-methyl psychotrine, emetamine, cephaeline isoamyl ether, cephaeline ethyl ether, dehydroemetine, or a prodrug, metabolite, or derivative of any of the foregoing, or a pharmaceutically acceptable salt of any of the foregoing.

Embodiment 29. The composition of embodiment 27, wherein at least one emetine compound of the combination comprises a compound in Table 1, or a prodrug, metabolite, or derivative of any of the foregoing, or a pharmaceutically acceptable salt of any of the foregoing.

Embodiment 30. The composition of embodiment 27, wherein at least one emetine compound of the combination comprises emetine or an emetine derivative having the structure of Formula 1 or Formula 2:

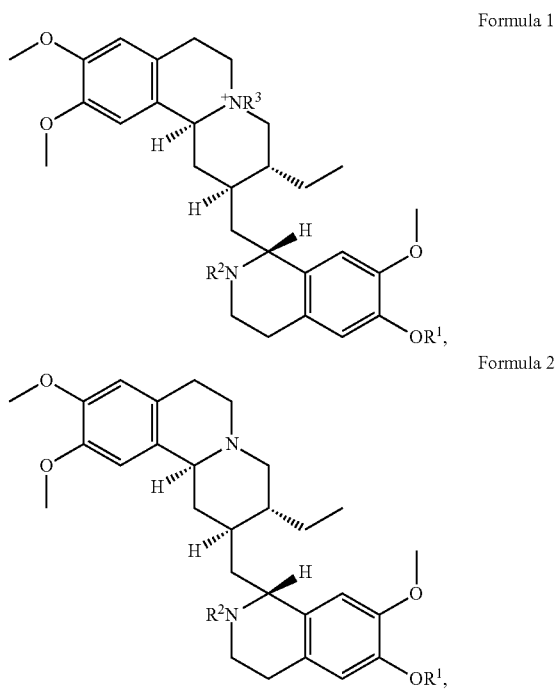

Formula 1

Formula 2 or a pharmaceutically acceptable salt of Formula 1 or Formula 2, where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2$R where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2$NR'R" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —P(O)OR'OR" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

Embodiment 31. The composition of embodiment 27, wherein the combination does not comprise emetine.

Embodiment 32. A composition comprising at least one emetine compound; and an additional agent effective for the treatment of one or more symptoms of Flavivirus infection.

Embodiment 33. The composition of embodiment 32, wherein the at least one emetine compound comprises emetine, cephaeline, psychotrine, o-methyl psychotrine, emetamine, cephaeline isoamyl ether, cephaeline ethyl ether, dehydroemetine, or a prodrug, metabolite, or derivative of any of the foregoing, or a pharmaceutically acceptable salt of any of the foregoing.

Embodiment 34. The composition of embodiment 32, wherein the at least one emetine compound comprises a compound in Table 1, or a prodrug, metabolite, or derivative of any of the foregoing, or a pharmaceutically acceptable salt of any of the foregoing.

Embodiment 35. The composition of claim 32, wherein the at least one emetine compound comprises emetine or an emetine derivative having the structure of Formula 1 or Formula 2:

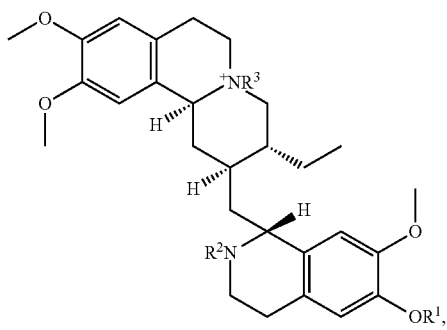

Formula 1

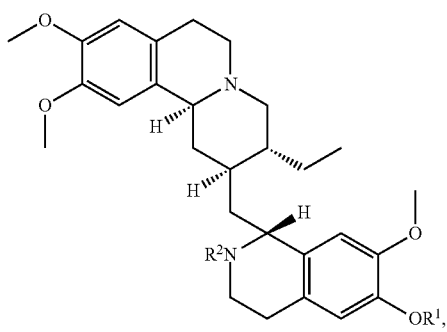

Formula 2 or a pharmaceutically acceptable salt of Formula 1 or Formula 2, where $R^1$ and $R^2$, are independently selected from the group consisting of: H; $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl; $C_2$-$C_{13}$ heterocycle with one to four heteroatoms selected from O, S, and N and is saturated, unsaturated, aromatic or any combination thereof; $C_7$-$C_{20}$ alkylaryl; COOR, where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof; or $C_7$-$C_{20}$ alkylaryl; C(O)R' where R' is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl; $C_6$-$C_{14}$ aryl, $C_2$-$C_{13}$ heterocycle with one to four heteroatoms selected from O, S, and N and is saturated, unsaturated, aromatic or any combination thereof; $C_7$-$C_{20}$ alkylaryl, CONR'R", where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer, $C_6$-$C_{14}$ aryl, or $C_7$-$C_{20}$ alkylaryl or where R' and R" are combined into a 4- to 8-membered ring cyclic, uninterrupted or interrupted with O, S, or NR where R is H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; SOR where R is $C_1$-$C_9$ alkyl of any isomer, ($C_2$-$C_9$) alkenyl where the double bond is at any position in the alkenyl carbon chain and of any conformational isomer, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2$R where R is $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —$SO_2$NR'R" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; —P(O)OR'OR" where R' and R" are independently H, $C_1$-$C_9$ alkyl of any isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, ($C_2$-$C_9$) alkenyl where the double bond is at any position in the alkenyl carbon chain and of any conformational isomer and is acyclic or cyclic and is uninterrupted or interrupted with O, S, or NR where R is H, $C_1$-$C_9$ alkyl of any isomer, ($C_2$-$C_9$) alkenyl where the double bond is at any position in the alkenyl carbon chain and of any conformational isomer, $C_6$-$C_{14}$ aryl, or $C_7$-$C_{20}$ alkylaryl, $C_6$-$C_{14}$ aryl, $C_2$-$C_{13}$ heterocycle with one to four heteroatoms selected from O, S, and N and is saturated, unsaturated, aromatic or any combination thereof, or $C_7$-$C_{20}$ alkylaryl; and where $R^3$ is $C_1$-$C_9$ alkyl of any isomer $C_2$-$C_{13}$ heterocycle with one to four heteroatoms selected from O, S, and N and is saturated, unsaturated, aromatic or any combination thereof, ($C_2$-$C_9$) alkenyl where the double bond is at any position in the alkenyl carbon chain and of any conformational isomer $C_2$-$C_{13}$ heterocycle with one to four heteroatoms selected from O, S, and N and is saturated, unsaturated, aromatic or any combination thereof, $C_6$-$C_{14}$ aryl, or $C_7$-$C_{20}$ alkylaryl.

Embodiment 36 . The composition of any preceding embodiment, wherein the at least one emetine compound does not comprise emetine.

Embodiment 37 . A compound having a structure shown in Table 1, cephaeline isoamyl ether, cephaeline ethyl ether, dehydroemetine or a prodrug, metabolite, derivative, or pharmaceutically acceptable salt thereof.

Embodiment 38 . A composition comprising one or more compounds of embodiment 37; and a pharmaceutically acceptable carrier.

Definitions

The terms "compounds of the invention" or "compounds of the present invention" (unless specifically identified otherwise), and grammatical variations thereof, refer to the compounds and classes of compounds disclosed herein, such as emetine, cephaeline, psychotrine, o-methyl psychotrine, emetamine, cephaeline isoamyl ether, cephaeline ethyl ether, dehydroemetine, a compound of Table 1, a compound having the structure of Formula 1 or Formula 2 described herein, or a prodrug, metabolite, or derivative of any of the foregoing, or a pharmaceutically acceptable salt of any of the foregoing (e.g., hydrochloride salt or dihycrochloride salt), as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

The term "a," "an," "the" and similar terms used in the context of the present invention (especially in the context of the claims) are to be construed to cover both the singular and plural unless otherwise indicated herein or clearly contradicted by the context. Thus, for example, reference "a cell" or "a compound" should be construed to cover both a singular cell or singular compound and a plurality of cells and a plurality of compounds unless indicated otherwise or clearly contradicted by the context.

The term "agent" refers to all materials that may be used as or in a pharmaceutical composition, or that may be a compound such as small synthetic or naturally derived organic compounds, nucleic acids, polypeptides, antibodies, fragments, isoforms, variants, or other materials that may be used independently for such purposes.

The term "small molecule" refers to a composition that has a molecular weight of less than about 3 kilodaltons (kDa), less than about 1 kDa, or less than about 1 kDa. Small molecules may be nucleic acids, peptides, polypeptides, peptidomimetics, carbohydrates, lipids, or other organic (carbon-containing) or inorganic molecules. A "small organic molecule" is an organic compound (or organic compound complexed with an inorganic compound (e.g., metal), that has a molecular weight of less than about 3 kDa, less than about 1.5 kDa, or less than about 1 kDa.

The term "isolated," when used as a modifier of a composition of matter, such as a compound, means that the compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide). The compounds of the invention may be in isolated or substantially pure form.

The present invention includes derivatives of identified compounds, also referred to herein as pharmaceutically active derivatives. "Pharmaceutically active derivative" refers to any compound that upon administration to the subject or cell, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting Flavivirus (e.g., Zika virus) inhibitory activity and/or protective activity against effects of Flavivirus (e.g., Zika virus) that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g., by oxidation, reduction, hydrolysis or the like, each of which is carried out enzymatically. These compounds can be produced from compounds of the invention according to well-known methods. The term "indirectly" also encompasses metabolites of compounds according to the invention. Chemical reactions, reactants, and reagents useful for making derivatives can be found, for example, in *March's Advanced Organic Chemistry*, $7^{th}$ edition, 2013, Michael B. Smith, which is incorporated herein by reference in its entirety.

The term "metabolite" refers to all molecules derived from any of the compounds according to the invention in a cell or organism, preferably mammal. Pharmaceutically active metabolites of the compounds of the invention may be administered to a subject or contacted with a cell in vitro or in vivo.

The term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, *Pharmaceuticals,* 2009, 2(3):77-81, which is incorporated by reference herein in its entirety).

Pharmaceutical formulations include "pharmaceutically acceptable" and "physiologically acceptable" carriers, diluents or excipients. As used herein the terms "pharmaceutically acceptable" and "physiologically acceptable" carriers, dilutents, or excipients include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions. The phrase "pharmaceutically acceptable" indicates that the substance or composition must be compatible chemically and/or toxicologically, with the other ingredients comprising a formulation, and/or the mammal and/or cells being treated therewith. Examples of pharmaceutically acceptable carriers include but are not limited to saline, buffered saline, isotonic salinle, Ringer's solultion, dextrose, sterile water, deionized water, glycerol, ethanol, 5% dextrose in water, propylene glycol, and combinations of two or more of the foregoing.

The phrase "effective amount", in the context of a subject, means an amount of at least one compound of the invention that (i) treats or prevents the particular disease, condition, or disorder (e.g., Zika or other Flavivirus infection) in a subject, (ii) attenuates, ameliorates, or eliminates one or more symptoms of the particular disease, condition, or disorder (e.g., Zika or other Flavivirus infection) in a subject, or (iii) prevents or delays the onset of one or more symptoms of the particular disease, condition, or disorder described herein (e.g., Zika or other Flavivirus infection) in a subject.

The phrase "effective amount", in the context of a cell in vitro or in vivo, means an amount of at least one compound of the invention that (i) treats or prevents the particular disease, condition, or disorder (e.g., Zika or other Flavivirus infection) in a cell, (ii) attenuates, ameliorates, or eliminates one or more effects of the particular disease, condition, or disorder (e.g., Zika or other Flavivirus infection) in a cell, or (iii) prevents or delays the onset of one or more effects of the particular disease, condition, or disorder described herein (e.g., Zika or other Flavivirus infection) in a subject.

As used herein, a subject is "in need of" a treatment if such human or non-human animal subject would benefit biologically, medically or in quality of life from such treatment (preferably, a human). In some embodiments, the subject has a Flavivirus infection and is in need of therapy. In other embodiments, the subject does not have a Flavivirus infection and is in need of prophylaxis. In some embodiments, the subject in need of prophylaxis is at risk of becoming infected with the Flavivirus. In some embodiments, the subject is at increased risk of becoming infected with the Flavivirus relative to others in the population. In some embodiments, the subject is suspected to have a Flavivirus infection.

As used herein, the term "inhibit", "inhibition" or "inhibiting" refers to the reduction or suppression of a given condition, symptom, or disorder, or disease (e.g., Zika virus or other Flavivirus infection, or Zika viral or other Flavivirus load or titer), or a significant decrease in the baseline activity of a biological activity or process (inhibits or suppresses Zika or other Flavivirus infection, or inhibits or suppresses Zika or other Flavivirus replication, or inhibits or suppresses Zika-induced or other Flavivirus-induced neural cell death.

As used herein, the terms "subject", "patient", and "individual" refer to a human or non-human animal. Typically, the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. The subject may be any age or gender. For example, in some embodiments, the subject is a female. In some embodiments, the subject is a post-pubescent female or a post-pubescent female. In some embodiments, the subject is a pregnant female; in other embodiments, the subject is a non-pregnant female.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

As used herein, the term "contacting" in the context of contacting a cell with at least one compound of the invention in vitro or in vivo means bringing at least one compound into contact with the cell, or vice-versa, or any other manner of causing the compound and the cell to come into contact. In those embodiments of the method for inhibiting Flavivirus infection in human or non-human animal cells in vitro or in vivo, when a cell is contacted with a compound in vivo, the compound is administered to a subject, and the administration may occur by any route (e.g., topical, oral, parenteral, subcutaneous, transdermal, transbuccal, intravascular (e.g., intravenous or intra-arterial), intramuscular, subcutaneous, intranasal, and intra-ocular administration).

The compounds of the present invention can be formulated into pharmaceutically-acceptable salt forms. Pharmaceutically-acceptable salts of the compounds of the invention can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts. For example, in some embodiments, the emetine compound, such as emetine or cephaeline, is in the form of a hydrochloride salt or dihycrochloride salt.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods

Cell Line Cultures. The glioblastoma SNB-19 cell line (part of the National Cancer Institute 60 human tumor cell line) was a gift from Dr. David Meckes (Florida State University, Tallahassee, Fla.). SNB-19 cells were maintained at 37° C. in 5% $CO_2$ in RPMI-60, 1× penicillin/streptomycin, and 10% fetal bovine serum (Invitrogen). The *Aedes albopictus* C6/36 cell line (ATCC) was maintained at 28° C. in 5% $CO_2$.

Preparation of ZIKV and Cell Infection. The MR766-ZIKV stock with the titer of $1\times10^5$ Tissue Culture Infective Dose (TCID)/ml in the form of culture fluid from an infected rhesus *Macaca* cell line LLC-MK2, was originally obtained from ZeptoMetrix (Buffalo, N.Y.). The FSS13025-ZIKV strain was obtained from Drs. Robert Tesh and Pei-Yong Shi (University of Texas Medical Branch, Galveston, Tex.). The PRVABC59 strain was obtained from ATCC (Manassas, Va.). Original viral stocks were then amplified in *Aedes albopictus* clone C6/36 cells. Briefly, C6/36 cells were inoculated with viral inoculum for one hour at 28° C. in low volume of media (3 ml per T-75 flask), with rocking every 15 minutes, before addition of 17 ml media. Viral inoculated cells were incubated at 28° C. for 6-7 days before harvesting of supernatant. C6/36-amplified ZIKV titer was determined by infecting Vero cells for 48 hours with a methyl-cellulose overlay and analyzed for focus-forming units per mL (FFU/ml). In mock infections, an equal volume of spent uninfected C6/36 culture medium was used. For infections, cells were seeded into 12-well plates with/without coverslips one day prior to virus addition. For all cell types, compound was added 1 hour prior to viral addition unless otherwise specified. Cells were harvested at 24-72 hours post-infection.

Immunocytochemistry. Cells were fixed with 4% paraformaldehyde (Sigma) for 15 min at room temperature. Samples were permeabilized and blocked with 0.25% Triton X-100 (Sigma) and 10% donkey or goat serum in PBS for 20 min as previously described (Chiang et al., 2011; [41]; Yoon et al., 2014). Samples were then incubated with primary antibodies at 4° C. overnight, followed by multiple PBST washes and incubation with secondary antibodies for 1 h at room temperature. Slides were mounted using VECTASHIELD with DAPI (Vectorlabs, Burlingame, Calif.). The following primary antibodies were used: anti-flavivirus group antigen (clone D1-4G2-4-15; mouse; 1:500; Millipore), and anti-cleaved caspase-3 (Asp15; Rabbit; 1:500; Cell Signaling Technology). Antibodies were prepared in PBS containing 0.25% Triton X-100 and 10% donkey serum. Images were taken by Zeiss LSM 700 and 880 confocal microscopes, Olympus BX61, or Zeiss Axiovert 200M microscope.

Western Blot. Cells were harvested by trypsinization, pelleting, and subsequent lysis in 1x Laemlli buffer and boiled, or directly lysed in 1x Laemlli buffer and boiled. Antibodies used were anti-ZIKV NS1 (1:2000; BF-1225-36, BioFront Technologies, Tallahassee, Fla.) or GAPDH (Santa Cruz Biotechnology, Texas).

NS1 ELISA. The anti-ZIKV NS1 ELISA (ZKV-NS1-EK) was obtained from BioFront Technologies (Tallahassee, Fla.) and used according to the manufacturer's protocol.

Data Analysis and Statistics. The primary screen data and curve fitting were analyzed using software developed internally [17]. The concentration-response curves and $IC_{50}$ values of compound confirmation data were calculated using Prism software (GraphPad Software, Inc. San Diego, Calif.). All values are expressed as the mean+/−SD (n≥3) unless it was specified. Western blots and IFA images were quantified using ImageJ (NIH, Bethesda, Md.).

EXAMPLE 1

Identification of Emetine as an Anti-Zika Virus Compound

The inventors identified the compound emetine, an alkaloid obtainable from ipecac root or ipecacuanha, from a library of compounds used in a large scale compound screen measuring cell-death inhibition in ZIKV infected cells. Each compound having both a NS1 $IC_{50}$ value below $10^{-6}$ M (1 uM) and a ratio of Toxicity $IC_{50}$ (cell-killing activity) to NS1 $IC_{50}$ (virus-inhibiting activity) of 4 or greater was selected as an effective compound.

A one-step NS1 TR-FRET (Time-resolved fluorescence resonance energy transfer) assay for a screen of anti-ZIKV compounds was carried out. Human embryonic kidney cell line HEK293 cells were seeded into 384-well plates and infected with ZIKV MR766 at a MOI of 0.5 for 2 days. The FRET assay was performed with two clones of anti-NS1 antibody (ab) differentially labelled with donor and acceptor fluorophores. Different combinations of antibody dilutions were tested to achieve high and producible signal to noise ratios.

Because this assay is measuring NS1, which a virally-encoded protein, this screen is focused on compounds that have antiviral activities as opposed to compounds that can block ZIKV-induced cell death. The advantage of this FRET assay over the NS1 ELISA assay [47] is it has been adapted to the 384-well format and does not require a washing step. These are advantages as a screening assay.

Each compound having both a NS1 $IC_{50}$ value below $10^{-6}$ M (1 uM) and a ratio of Toxicity $IC_{50}$ (cell-killing activity) to NS1 $IC_{50}$ (virus-inhibiting activity) of 4 or greater was selected as an effective compound. The results from emetine are shown in Table 2.

TABLE 2

| Name | NS1-IC50 | Tox IC50 | Tox IC50/NS1 IC50 ratio |
| --- | --- | --- | --- |
| Emetine | 1.14E−07 | No | |

The chemical structure of emetine is shown below.

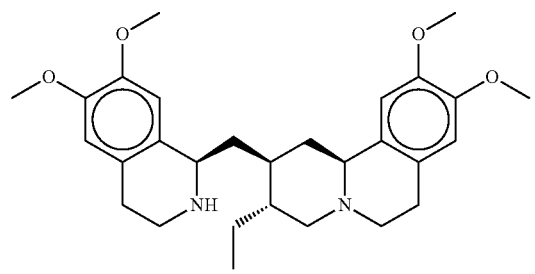

Figure 7:
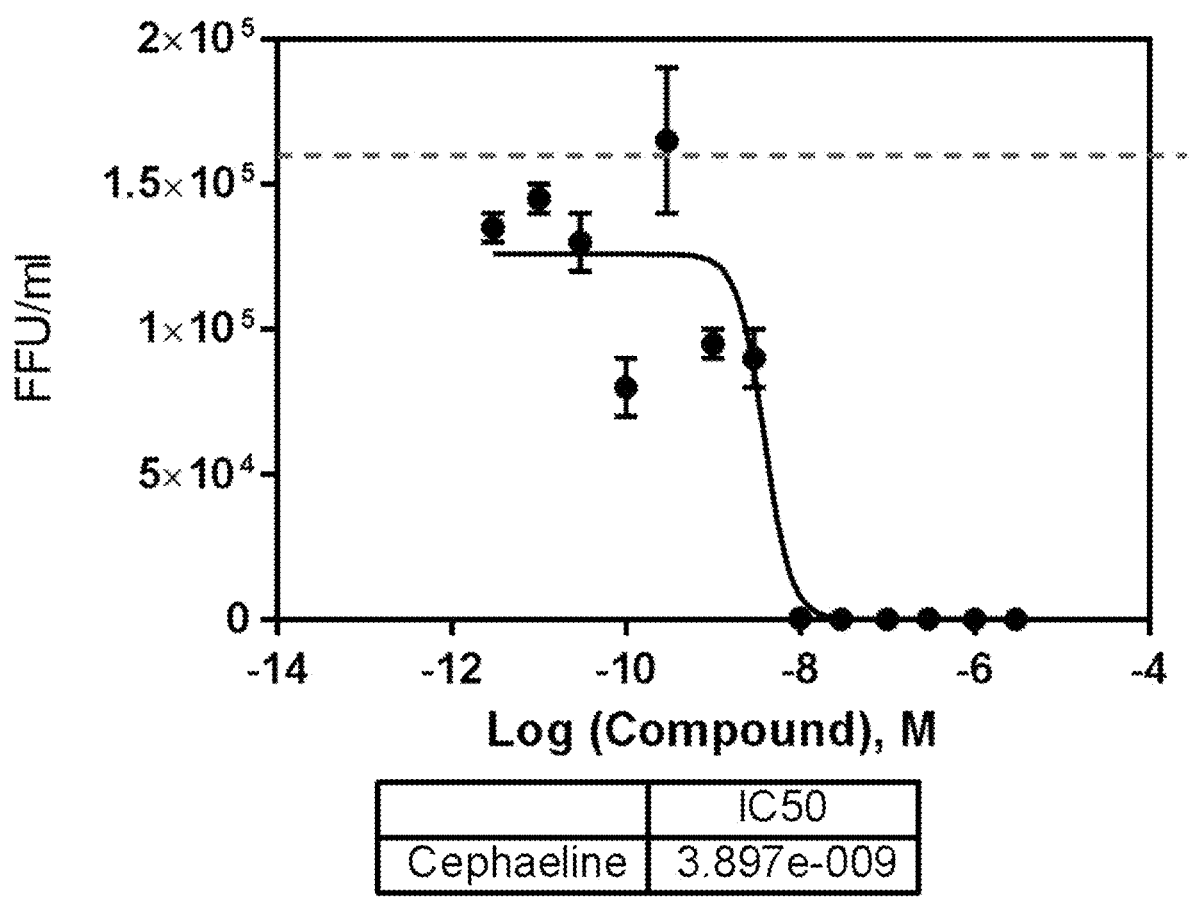
FIG. 7. Antiviral activity of cephaeline against ZIKV infection. ZIKV production from human glioblastoma SNB-19 cells treated with increasing concentrations of cephaeline. 24 hours post-infection, supernatants from SNB-19 cells were titrated onto naïve Vero cells plated in a monolayer in 96-well plates for infectious focus-forming unit assay as previously described and focus forming units quantified [10].

Anti-Zika virus activities of emetine and cephaeline (another alkalkoid and desmethyl analog of emetine, obtainable from ipecac root) were further evaluated. Results for emetine are shown in FIGS. 1A-B, 2A-B, 3, 4, 5, and 6A-B. Results for cephaeline are shown in FIG. 7.

EXAMPLE 2

Emetine Inhibits Zika Virus In Vivo in a Dose-dependent Manner

Animal models useful for Zika virus have been reported in the literature (see, for example, Morrison T E et al., *J. Virol.*, 2017, "Animal Models of Zika Virus Infection, Pathogenesis, and Immunity," 91(8):1-15; Dowall S. Dak. et al., PLOS Neglected Tropical Diseases, 2016, "A Susceptible Mouse Model for Zika Virus Infection," 10(5): e0004658; Koid F et al., *Front Microbiol.*, 2016, "Development of a Zika Virus Infection Model in Cynomolgus Macaques," 7: 2028; Dudley D M et al., *Nat Commun.*, 2016, "A rhesus macaque model of Asian-lineage Zika virus infection," 28; 7:12204, which are incorporated herein by reference in their entirety.

Mice homozygous for the Ifnar1− null allele lack type-I interferon receptor function, resulting in reduced immune response and increased susceptibility to viral infection. These mice may be useful in studying antiviral immune responses, as well as interferon stimulation and JAK-STAT signaling. Mouse mutants involving this gene have been used in studies of Zika virus pathogenesis (Dowall S. Dak. et al., "A susceptible mouse model for Zika virus infection," *PloS Negl. Trop. Dis.*, 2016, 10:e0004658; Lazear H M et al., "A mouse model of Zika virus pathogenesis," *Cell Host Microbe*, 2016, 19:720-730; and Rossi S L et al., "Characterization of a novel murine model to study Zika virus," *Am. J. Trop. Med., Hyg.*, 2016, 94:1362-1369).

Figure 8:
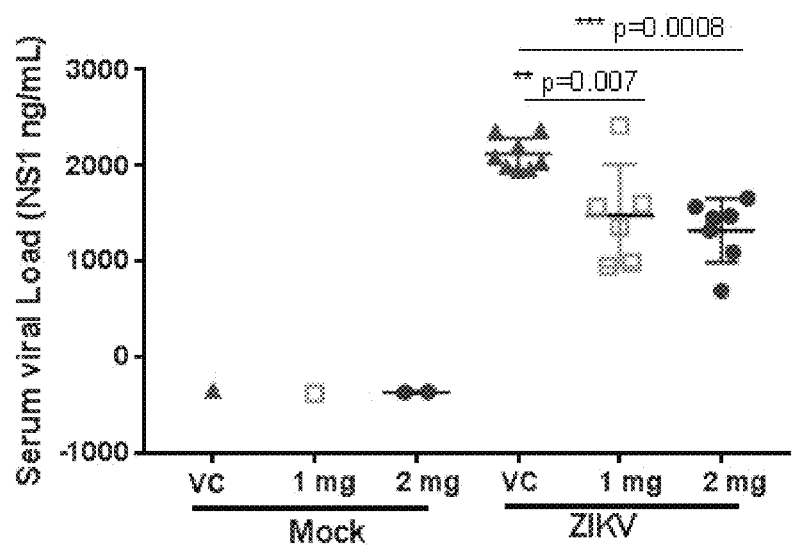
FIG. 8. Zika virus load estimation in mouse serum following emetine treatment. Serum was separated. NS1 protein was estimated using ZIKV-NS1 ELISA kit (Biofront, Tallahassee, Fla.) as per the manufacturer's protocol. Briefly, 5 μl of the serum was lysed with equal volume of lysis buffer for 30 min at 37° C. A 1:900 dilution of the serum was done using sample dilution buffer and added to ELISA plates. Reactions were quantified using HRP conjugated antibody and TMB. Absorbance was taken at 450 nm after adding the stop solution. Statistical analysis was done using the Mann-Whitney ANOVA. *p<0.05, p<0.01, *p<0.001.

Ifnar1−/− mice (7-8 wk old, male and female, Jackson Lab) were dosed (i.p) with Emetine 1 mg/kg/day (n=6), 2 mg/kg/day (n=8) or saline (Vehicle control, n=8) starting at 24 hours prior to challenging with ZIKV ($10^3$, Focal forming unit (FFU)) on day 0. Drug was continued until day 6. At peak viremia (day 3), a blood sample was taken from the tail vein and serum was separated and stored at −70° C. till further analysis. The body weight were monitored twice daily until day 10. Mice reaching humane end points were euthanized. With emetine treatment, there was a 30% and 37% decrease in serum viral load with 1 mg/kg and 2 mg/kg treatment, respectively. Results are shown in FIG. 8.

EXAMPLE 3

Pre-Challenge and Post-Challenge Treatment with Emetine Inhibits Zika Virus In Vivo Ifnar1−/− mice (8 wk old, male and female) were dosed with Emetine 2 mg/kg/day i.p. starting at 24 hours prior (n=8) or 24 after (n=7) the challenging with ZIKV on day 0. Drug was continued till day 3. Mice were euthanized, and blood and liver tissue were collected.

Figure 9:
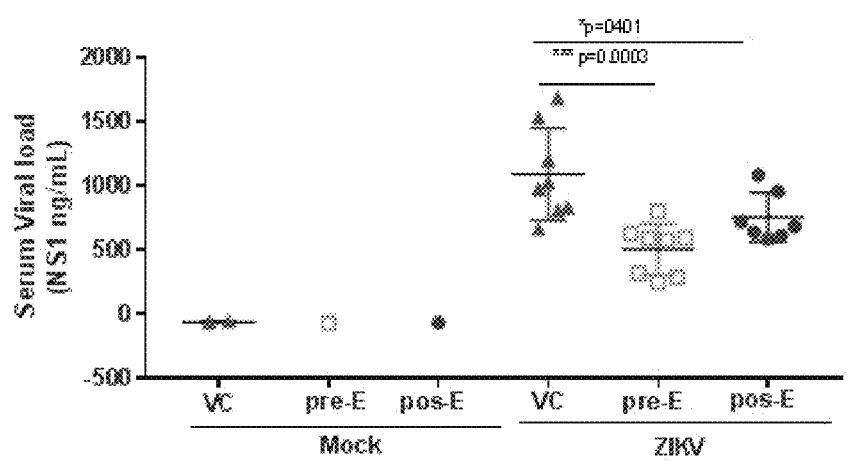

There was a 55% and 32% reduction in serum viral load with emetine dihydrochloride dosed 2 mg/kg starting at 24 hours prior and 24 hours after the ZIKV challenge, respectively. Results are shown in FIG. 9.

Figure 10:
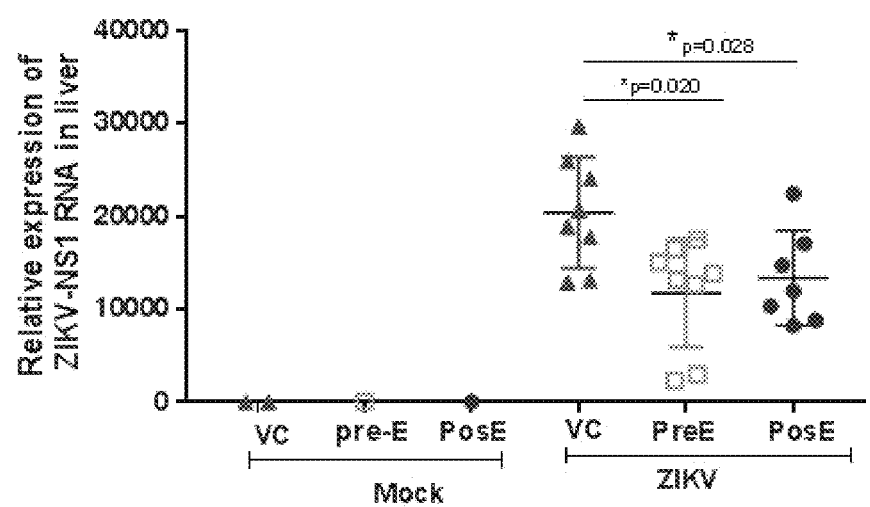

There was 42% and 35% reduction in liver viral load with emetine dihydrochloride dosed 2 mg/kg starting at 24 hours prior and after the ZIKV challenge, respectively. Results are shown in FIG. 10.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. Nos. 5,323,907, 5,052,558 and 5,033,252
U.S. Patent Publication 2014/0148377
U.S. Patent Publication 20150210712
U.S. Patent Publication 2017/0190700
International Patent Publication WO 2009/143297
International Patent Publication WO 2016/004166
1. Dick, G. W., Kitchen, S. F. & Haddow, A. J. Zika virus. I. Isolations and serological specificity. Trans R Soc Trop MedHyg 46, 509-520 (1952).
2. Duffy, M. R., et al. Zika virus outbreak on Yap Island, Federated States of Micronesia. *N Engl J Med* 360, 2536-2543 (2009).
3. Cao-Lormeau, V. M., et al. Zika virus, *French polynesia, South pacific,* 2013. *Emerg Infect Dis* 20, 1085-1086 (2014).
4. Musso, D. Zika Virus Transmission from French Polynesia to Brazil. *Emerg Infect Dis* 21, 1887 (2015).
5. Heymann, D. L., et al. Zika virus and microcephaly: why is this situation a PHEIC? *Lancet* 387, 719-721 (2016).
6. Mlakar, J., et al. Zika Virus Associated with Microcephaly. *N Engl J Med* 374, 951-958 (2016).
7. Rasmussen, S. A., Jamieson, D. J., Honein, M. A. & Petersen, L. R. Zika Virus and Birth Defects—Reviewing the Evidence for Causality. *N Engl J Med* 374, 1981-1987 (2016).
8. Cao-Lormeau, V. M., et al. Guillain-Barré Syndrome outbreak associated with Zika virus infection in French Polynesia: a case-control study. *Lancet* 387, 1531-1539 (2016).
9. Araujo, L. M., Ferreira, M. L. & Nascimento, O. J. Guillain-Barré syndrome associated with the Zika virus outbreak in Brazil. Arq Neuropsiquiatr 74, 253-255 (2016).
10. Xu et al. Identification of small-molecule inhibitors of Zika virus infection and induced neural cell death via a drug repurposing screen. *Nature Medicine,* 22(10):1101-1110 (2016).
Berge S. M. et al., "Pharmaceutical Salts," *Journal of Pharmaceutical Science,* 66:1-19 (1997) Chiang et al., 2011
Dowall S D et al., "A susceptible mouse model for Zika virus infection," *PloS Negl. Trop. Dis.,* 2016, 10(5): e0004658
Dudley D M et al., *Nat Commun.,* 2016, "A rhesus macaque model of Asian-lineage Zika virus infection," 28; 7:12204
Elgart A et al., "Improved oral bioavailability of BCS class 2 compounds by self nano-emulsifying drug delivery systems (SNEDDS): the underlying mechanisms for amiodarone and talinolol", *Pharm Res.,* 2013 December; 30(12):3029-44
Elkihel L et al., "Synthesis and orally macrofilaricidal evaluation of niclosamide lymphotropic prodrugs," *Arzneimittelforschung,* 1994, 44(11): 1259-64
Gourinat A-C et al. (2015) *Emerg Infect Dis,* vol. 21, no. 1, pp. 84-86
Kansara H. et al., "Techniques used to enhance bioavailability of BCS class II drugs: a review," *Int. J. Drug Dev. & Res.,* 2015, 7(1):82-93
Khamkar G S, "Self micro emulsifying drug delivery system (SMEED) o/w microemulsion for BCS Class II drugs: an approach to enhance oral bioavailability," *International Journal of Pharmacy and Pharmaceutical Sciences,* 2011, 3(3):1-3
Koid F et al., *Front Microbiol.,* 2016, "Development of a Zika Virus Infection Model in Cynomolgus Macaques," 7: 2028
Kuno G et al., *Journal of Virology,* 1998, "Phylogeny of the Genus Flavivirus," 72(1):73-83
Lasslo A et al., "Chemical and Pharmacologic Studies on Emetine and Quaternary Emetine Derivatives," *Journal of Pharmaceutical Sciences,* January 1950, 39(1):43-46
Lazear H M et al., "A mouse model of Zika virus pathogenesis," *Cell Host Microbe,* 2016, 19:720-730
Morrison T E et al., *J. Virol.,* 2017, "Animal Models of Zika Virus Infection, Pathogenesis, and Immunity," 91(8):1-15
Musso D et al. (2015)*J Clin Virol,* vol. 68, pp. 53-55
Pyman F L et al., "The Action of Certain Emetine Derivatives on Amoebae," *Journal of Pharmacology and Experimental Therapeutics,* October 1917, 10(4):237-241
Reddy M S et al., "Solubility enhancement of fenofibrate, a BCS class II drug, by self emulsifying drug delivery systems," *International Research Journal of Pharmacy,* 2011, 2(11):173-177
Rossi S L et al., "Characterization of a novel murine model to study Zika virus," *Am. J. Trop. Med., Hyg.,* 2016, 94:1362-1369
Singh N. et al. "Techniques for bioavailability enhancement of BCS class II drugs: a review," *International Journal of Pharmaceutical and Chemical Science,* 2013, 2(2):1092-1101
Smith, Michael B. *March's Advanced Organic Chemistry,* 7$^{th}$ edition, 2013
Wu, Kuei-Meng, "A New Classification of Prodrugs: Regulatory Perspectives, *Pharmaceuticals,* 2009, 2(3):77-81
Yoon et al., 2014

We claim:

1. A method for treating or delaying the onset of Zika virus infection in a human or non-human animal subject, said method comprising administering an effective amount of cephaeline, or a pharmaceutically acceptable salt thereof, to a subject in need thereof.

2. The method of claim 1, wherein the subject has the Zika virus infection at the time of said administering, and the cephaeline, or pharmaceutically acceptable salt thereof, is administered as therapy.

3. The method of claim 2, further comprising, prior to said administering, identifying the subject as having the Zika virus infection.

4. The method of claim 3, wherein said identifying comprises assaying a biological sample obtained from the subject for the presence of Zika virus nucleic acids or Zika virus proteins.

5. The method of claim 4, wherein said assaying comprises use of reverse transcriptase-polymerase chain reaction (RT-PCR), immunological assay, or Plaque-reduction neutralization testing (PRNT).

6. The method of claim 1, wherein the subject does not have the Zika virus infection at the time of said administering, and the cephaeline, or pharmaceutically acceptable salt thereof, is administered to delay onset of the Zika virus infection.

7. The method of claim 1, wherein the cephaeline, or pharmaceutically acceptable salt thereof, is administered orally, nasally, rectally, parenterally, subcutaneously, intramuscularly, or intravascularly.

8. The method of claim 1, further comprising administering an additional agent for treating or delaying the onset of Zika virus infection, or a symptom thereof, in the same formulation as the cephaeline or pharmaceutically acceptable salt thereof, or in a separate formulation before, during, or after administration of the cephaeline or pharmaceutically acceptable salt thereof.

9. A method for inhibiting Zika virus infection in human or non-human animal cells in vitro or in vivo, said method comprising contacting an effective amount of cephaeline, or a pharmaceutically acceptable salt thereof, to a human or non-human animal cell in vitro or in vivo before or after exposure of the cell to Zika virus.

10. The method of claim 1, wherein the subject is a human.

11. The method of claim 9, wherein the cell is a human cell.

12. The method of claim 9, wherein said contacting is carried out in vitro.

13. The method of claim 9, wherein said contacting is carried out in vivo.

14. The method of claim 9, wherein said contacting is carried out before exposure of the cell to the Zika virus.

15. The method of claim 9, wherein said contacting is carried out after exposure of the cell to the Zika virus.

* * * * *

UNITED STATES PATENT AND TRADEMARK OFFICE
CERTIFICATE OF CORRECTION

Page 1 of 1

PATENT NO. : 10,555,942 B2
APPLICATION NO. : 16/156124
DATED : February 11, 2020
INVENTOR(S) : Hengli Tang et al.

It is certified that error appears in the above-identified patent and that said Letters Patent is hereby corrected as shown below:

In the Specification

Column 1,
Line 14, Insert --GOVERNMENT SUPPORT
This invention was made with government support under NS047344 and NS097370 awarded by the National Institutes of Health. The government has certain rights in the invention.--.

Column 61,
Line 54, "salinle," should read --saline,--.
Line 55, "solultion," should read --solution,--.

Column 63,
Line 27, "dihycrochloride" should read --dihydrochloride--.

Signed and Sealed this
Fourth Day of August, 2020

Andrei Iancu
*Director of the United States Patent and Trademark Office*